US008466160B2

(12) United States Patent
Rikova et al.

(10) Patent No.: US 8,466,160 B2
(45) Date of Patent: Jun. 18, 2013

(54) IDENTIFICATION OF NON-SMALL CELL LUNG CARCINOMA (NSCLC) TUMORS EXPRESSING PDGFR-ALPHA

(75) Inventors: Klarisa Rikova, Reading, MA (US); Roberto Polakiewicz, Lexington, MA (US); Ailan Guo, Lexington, MA (US); Katherine Eleanor Crosby, Middleton, MA (US); Qingfu Zeng, Hamilton, MA (US); Kimberly A Lee, Seattle, WA (US)

(73) Assignee: Cell Signaling Technology, Inc., Danvers, MA (US)

( * ) Notice: Subject to any disclaimer, the term of this patent is extended or adjusted under 35 U.S.C. 154(b) by 0 days.

(21) Appl. No.: 12/982,490

(22) Filed: Dec. 30, 2010

(65) Prior Publication Data
US 2011/0195447 A1 Aug. 11, 2011

Related U.S. Application Data

(62) Division of application No. 11/174,051, filed on Jul. 1, 2005, now Pat. No. 7,932,044.

(51) Int. Cl.
*A01N 43/54* (2006.01)
*G01N 33/574* (2006.01)
*C12Q 1/68* (2006.01)

(52) U.S. Cl.
USPC .......... 514/256; 435/7.23; 435/6.14; 514/247

(58) Field of Classification Search
USPC .................. 435/6.14, 7.23; 514/247, 256
See application file for complete search history.

(56) References Cited

U.S. PATENT DOCUMENTS

| | | | |
|---|---|---|---|
| 7,932,044 B2 | 4/2011 | Rikova et al. | 435/7.1 |
| 2006/0084142 A1 | 4/2006 | Heinrich et al. | 435/69.1 |

OTHER PUBLICATIONS

Li, Yamashiro, Tseng, Chang, and Ferrara. Beta-endorphin omission analogs: dissociation of immunoreactivity from other biological activities. Proceedings of the National Academy of Sciences, 1980. vol. 77, pp. 3211-3214.*
Canadian Patent Office, Official Action—International Application No. CA 2,617,201, dated May 30, 2011 (2 pages).
Apperley et al., "Response to Imatinib Mesylate in Patients with Chronic Myeloproliferative Diseases with Rearrangements of the Platelet-Derived Growth Factor Receptor Beta," *N. Engl. J. Med.*, vol. 347, No. 7, pp. 481-487 (2002).
Fitzer-Attas et al., "Expression of functionally intact pdgf-α receptors in highly metastatic 3LL Lewis lung carcinoma cells," *International Journal of Cancer*, vol. 53, pp. 315-322 (1993).
Forsberg et al., "Expression of Functional PDGF beta Receptors in a Human Large-Cell Lung-Carcinoma Cell Line," *International Journal of Cancer*, vol. 53, No. 4, pp. 556-560 (1993).
Gazit et al., "Expression of the normal human *sis*/PDGF-2 coding sequence induces cellular transformation," *Cell*, vol. 39, No. 1, pp. 89-97 (1984).
Gerber et al., Absolute quantification of proteins and phosphoproteins from cell lysates by tandem MS, *Proc. Natl. Acad. Sci.*, vol. 100, pp. 6940-6945 (2003).
Heldin et al., "Mechanism of Action and In Vivo Role of Platelet-Derived Growth Factor," *Physiol. Rev.*, vol. 79, No. 4, pp. 1283-1316 (1999).
Ide et al., "Expression of colony-stimulating factor 1 receptor during prostate development and prostate cancer progression," *Proc. Natl. Acad. Sci.*, vol. 99, No. 22, pp. 14404-14409 (2002).
Laird et al., "Mechanism of Action and Biomarker Studies of SU11248, a Selective Oral Multi-Targeted Tyrosine Kinase Inhibitor With Anti-Tumor and Anti-Angiogenic Activity Through Targeting PDGFR, VEGFR, KIT and FLT3," *Proc. of the American Assoc. for Cancer Res.*, vol. 44, 2nd Ed., p. 937, Abstract #4716 (2003).
Mendel et al., "In vivo antitumor activity of SU11248, a novel tyrosine kinase inhibitor targeting VEGF and PDGFR: determination of a pharmacokinetic/pharmacodynamic relationship," *Clinical Cancer Research*, vol. 9, pp. 327-337 (2003).
Reinmuth, "Combined anti-PDGFR-.alpha. and PDGFR-.beta. targeting in non-small cell lung cancer," *Int. J. Cancer*, vol. 124, pp. 1535-1544 (2009).
Ross et al., "The biology of platelet-derived growth factor," *Cell*, vol. 46, No. 2, pp. 155-169 (1986).
Ross et al., "Platelet-derived growth factor—its role in health and disease," *Adv. Exp. Med. Bio.*, vol. 234, pp. 9-21 (1988).
Vassbotn et al., "Activated Platelet-Derived Growth Factor Autocrine Pathway Drives the Transformed Phenotype of a Human Glioblastoma Cell Line," *J. Cell Physiol.*, vol. 158, No. 2, pp. 381-389 (1994).
Vignaud et al., "The Role of Platelet-derived Growth Factor Production by Tumor-associated Macrophages in Tumor Stroma Formation in Lunch Cancer," *Cancer Res.*, vol. 54, No. 20, pp. 5455-5463 (1994).
Zhang et al., "Gleevac (STI-571) inhibits lung cancer cell growth (A549) and potentiates the cisplatin effect in vitro," *Mol. Cancer*, vol. 2, No. 1, pp. 1-10 (2003).
American Cancer Society, "Cancer Facts and Figures" (2003).
European Patent Office, Supplementary European Search Report—Application No. 05768977.0-1223, dated Sep. 3, 2009 (4 pages).
International Searching Authority, *International Preliminary Report on Patentability and Written Opinion of the International Searching Authority*—Application No. PCT/US2005/023858, dated Jan. 9, 2008 (4 pages).
International Search Report—Application No. PCT/US2005/023858, dated Nov. 27, 2006 (1 page).

\* cited by examiner

*Primary Examiner* — Stephen Rawlings
*Assistant Examiner* — Yan Xiao
(74) *Attorney, Agent, or Firm* — Sunstein Kann Murphy & Timbers LLP

(57) ABSTRACT

The invention discloses a previously unidentified subset of mammalian non-small cell lung carcinomas (NSCLC) in which platelet-derived growth factor receptor alpha (PDGFRα) is expressed and is driving the disease, and provides methods for identifying a mammalian NSCLC tumor that belongs to a subset of NSCLC tumors in which PDGFRα is expressed, and for identifying a NSCLC tumor that is likely to respond to a PDGFRα-inhibiting therapeutic. The invention also provides methods for inhibiting the progression of a mammalian NSCLC tumor in which PDGFRα is expressed, and for determining whether a compound inhibits the progression of a PDGFRα-expressing mammalian NSCLC tumor.

10 Claims, 12 Drawing Sheets
(6 of 12 Drawing Sheet(s) Filed in Color)

FIGURE 1.

```
         10         20         30         40         50         60
MGTSHPAFLV LGCLLTGLSL ILCQLSLPSI LPNENEKVVQ LNSSFSLRCF GESEVSWQYP 70         80         90        100        110        120
MSEEESSDVE IRNEENNSGL FVTVLEVSSA SAAHTGLYTC YYNHTQTEEN ELEGRHIYIY 130        140        150        160        170        180
VPDPDVAFVP LGMTDYLVIV EDDDSAIIPC RTTDPETPVT LHNSEGVVPA SYDSRQGFNG 190        200        210        220        230        240
TFTVGPYICE ATVKGKKFQT IPFNVYALKA TSELDLEMEA LKTVYKSGET IVVTCAVFNN 250        260        270        280        290        300
EVVDLQWTYP GEVKGKGITM LEEIKVPSIK LVYTLTVPEA TVKDSGDYEC AARQATREVK 310        320        330        340        350        360
EMKKVTISVH EKGFIEIKPT FSQLEAVNLH EVKHFVVEVR AYPPPRISWL KNNLTLIENL 370        380        390        400        410        420
TEITTDVEKI QEIRYRSKLK LIRAKEEDSG HYTIVAQNED AVKSYTFELL TQVPSSILDL 430        440        450        460        470        480
VDDHHGSTGG QTVRCTAEGT PLPDIEWMIC KDIKKCNNET SWTILANNVS NIITEIHSRD 490        500        510        520        530        540
RSTVEGRVTF AKVEETIAVR CLAKNLLGAE NRELKLVAPT LRSELTVAAA VLVLLVIVII 550        560        570        580        590        600
SLIVLVVIWK QKPRYEIRWR VIESISPDGH EYIYVDPMQL PYDSRWEFPR DGLVLGRVLG 610        620        630        640        650        660
SGAFGKVVEG TAYGLSRSQP VMKVAVKMLK PTARSSEKQA LMSELKIMTH LGPHLNIVNL 670        680        690        700        710        720
LGACTKSGPI YIITEYCFYG DLVNYLHKNR DSFLSHHPEK PKKELDIFGL NPADESTRSY 730        740        750        760        770        780
VILSFENNGD YMDMKQADTT QYVPMLERKE VSKYSDIQRS LYDRPASYKK KSMLDSEVKN 790        800        810        820        830        840
LLSDDNSEGL TLLDLLSFTY QVARGMEFLA SKNCVHRDLA ARNVLLAQGK IVKICDFGLA 850        860        870        880        890        900
RDIMHDSNYV SKGSTFLPVK WMAPESIFDN LYTTLSDVWS YGILLWEIFS LGGTPYPGMM 910        920        930        940        950        960
VDSTFYNKIK SGYRMAKPDH ATSEVYEIMV KCWNSEPEKR PSFYHLSEIV ENLLPGQYKK 970        980        990       1000       1010       1020
SYEKIHLDFL KSDHPAVARM RVDSDNAYIG VTYKNEEDKL KDWEGGLDEQ RLSADSGYII 1030       1040       1050       1060       1070       1080
PLPDIDPVPE EEDLGKRNRH SSQTSEESAI ETGSSSSTFI KREDETIEDI DMMDDIGIDS

SDLVEDSFL
```

Figure 3.

```
ORIGIN
        1 ttctccccgc cccccagttg ttgtcgaagt ctggggttg ggactggacc ccctgattgc
       61 gtaagagcaa aaagcgaagg cgcaatctgg acactgggag attcggagcg caggggagttt
      121 gagagaaact tttattttga agagaccaag gttgagggg ggcttatttc ctgacagcta
      181 tttacttaga gcaaatgatt agttttagaa ggatggacta taacattgaa tcaattacaa
      241 aacgcggttt ttgagcccat tactgttgga gctacaggga gagaaacagg aggagactgc
      301 aagagatcat ttgggaaggc cgtgggcacg ctctttactc catgtgtggg acattcattg
      361 cggaataaca tcggaggaga agtttcccag agctatgggg acttcccatc cggcgttcct
      421 ggtcttaggc tgtcttctca cagggctgag cctaatcctc tgccagcttt cattaccctc
      481 tatccttcca aatgaaaatg aaaaggttgt gcagctgaat tcatccttt ctctgagatg
      541 cttgggag agtgaagtga gctggcagta cccccatgtct gaagaagaga gctccgatgt
      601 ggaaatcaga aatgaagaaa acaacagcgg cctttttgtg acggtcttgg aagtgagcag
      661 tgcctcggcg gcccacacag ggttgtacac ttgctattac aaccacactc agacagaaga
      721 gaatgagctt gaaggcaggc acatttacat ctatgtgcca gacccagatg tagcctttgt
      781 acctctagga atgacggatt atttagtcat cgtggaggat gatgattctg ccattatacc
      841 ttgtcgcaca actgatcccg agactcctgt aaccttacac aacagtgagg gggtggtacc
      901 tgcctcctac gacagcagac agggcttaa tgggaccttc actgtagggc cctatatctg
      961 tgaggccacc gtcaaaggaa agaagttcca gaccatccca tttaatgttt atgctttaaa
     1021 agcaacatca gagctggatc tagaaatgga agctcttaaa accgtgtata agtcagggga
     1081 aacgattgtg gtcacctgtg ctgttttaa caatgaggtg gttgaccttc aatggactta
     1141 ccctggagaa gtgaaaggca aaggcatcaa aatgctggaa gaaatcaaag tcccatccat
     1201 caaattggtg tacactttga cggtccccga ggccacggtg aaagacagtg gagattacga
     1261 atgtgctgcc cgccaggcta ccagggaggt caaagaaatg aagaaagtca ctatttctgt
     1321 ccatgagaaa ggtttcattg aaatcaaacc caccttcagc cagttggaag ctgtcaacct
     1381 gcatgaagtc aaacattttg ttgtagaggt gcgggcctac ccacctccca ggatatcctg
     1441 gctgaaaaac aatctgactc tgattgaaaa tctcactgag atcaccactg atgtggaaaa
     1501 gattcaggaa ataaggtatc gaagcaaatt aaagctgatc cgtgctaagg aagaagacag
     1561 tggccattat actattgtag ctcaaaatga agatgctgtg aagagctata cttttgaact
     1621 gttaactcaa gttccttcat ccattctgga cttggtcgat gatcaccatg gctcaactgg
     1681 gggacagacg tgaggtgca cagctgaagg cacgccgctt cctgatattg agtggatgat
     1741 atgcaaagat attaagaaat gtaataatga aacttcctgg actatttgg ccaacaatgt
     1801 ctcaaacatc atcacggaga tccactcccg agacaggagt accgtggagg gccgtgtgac
     1861 tttcgccaaa gtggaggaga ccatcgccgt gcgatgcctg gctaagaatc tccttggagc
     1921 tgagaaccga gagctgaacga tggtggctcc caccctgcgt tctgaactca cggtgctgc
     1981 tgcagtcctg gtgctgttgg tgattgtgat catctcactt attgtcctgg ttgtcatttg
     2041 gaaacagaaa ccgaggtatg aaattcgctg gagggtcatt gaatcaatca gcccggatgg
     2101 acatgaatat atttatgtgg acccgatgca gctgccttat gactcaagat gggagttttcc
     2161 aagagatgga ctagtgcttg gtcgggtctt ggggtctgga gcgtttggga aggtggttga
     2221 aggaacagcc tatggattaa gccggtccca acctgtcatg aaagttgcag tgaagatgct
     2281 aaaacccacg gccagatcca gtgaaaaaca agctctcatg tctgaactga gataatgac
     2341 tcacctgggg ccacatttga acattgtaaa cttgctggga gcctgcacca agtcaggccc
     2401 catttacatc atcacagagt attgcttcta tggagatttg gtcaactatt gcataagaa
     2461 tagggatagc ttcctgagcc accacccaga gaagccaaag aaagagctgg atatctttgg
     2521 attgaaccct gctgatgaaa gcacacgag ctatgttatt ttatcttttg aaaacaatgg
     2581 tgactacatg gacatgaagc aggctgatac tacacagtat gtccccatgc tagaaaggaa
     2641 agaggtttct aaatattccg acatccagag atcactctat gatcgtccag cctcatataa
     2701 gaagaaatct atgttagact cagaagtcaa aaccctccttt tcagatgata actcagaagg
     2761 ccttactttt ttggatttgt tgagcttcac ctatcaagtt gcccgaggaa tggagttttt
     2821 ggcttcaaaa aattgtgtcc accgtgatct ggctgctcgc aacgtcctcc tggcacaagg
     2881 aaaaattgtg aagatctgtg actttggcct ggccagagac atcatgcatg attcgaacta
     2941 tgtgtcgaaa ggcagtacct ttctgccgt gaagtggatg gctcctgaga gcatctttga
     3001 caacctctac accacactga gtgatgtctg gtcttatggc attctgctct gggagatctt
     3061 ttcccttggt ggcaccccctt accccgagcat gatggtgact tctacttttct acaataagat
     3121 caagagtggg taccggatgg ccaagcctga ccacgtgtacc agtgaagtct acgagatcat
     3181 ggtgaaatgc tggaacagtg agccggagaa gagaccctcc ttttaccacc tgagtgagat
     3241 tgtggagaat ctgctgcctg gacaatataa aaagagttat gaaaaaattc acctggactt
     3301 cctgaagagt gaccatcctg ctgtggcacg catgcgtgtg gactcagaca atgcatacat
     3361 tggtgtcacc tacaaaaacg aggaagacaa gctgaaggac tgggagggtg tctggtgatga
     3421 gcagagactg agcgctgaca gtggctacac cattcctctg acattg acctgtccc
     3481 tgaggaggag gacctggca agaggaacag acacagctcg cagacctctg aagagagtgc
     3541 cattgagacg ggttccagca gttccacctt catcaagaga gaggacgaga ccattgaaga
     3601 catcgacatg atggacgaca tcggcataga ctcttcagac ctggtggaag acagcttcct
     3661 gtaactggcg gattcgaggg gttccttcca cttctgggc cacctctgga tcccgttcag
     3721 aaaaccactt tattgcaatg cggaggttga gaggaggact tggttgatgt ttaaagagaa
     3781 gttcccagcc aagggcctcg gggagcgttc taaatatgaa tgaatgggat attttgaaat
     3841 gaactttgtc agtgttgcct ctcgcagtca ctcagtagca tctcagtggt gtgtgaagtt
     3901 tggagataga tggataaggg aataataggc cacagaaggt gaactttgtg cttcaaggac
     3961 attggtgaga gtccaacaga cacaatttat actgcgacag aacttcagca ttgtaattat
```

Figure 3 (cont.)

```
4021 gtaaataact ctaaccaagg ctgtgtttag attgtattaa ctatcttctt tggacttctg
4081 aagagaccac tcaatccatc catgtacttc cctcttgaaa cctgatgtca gctgctgttg
4141 aacttttttaa agaagtgcat gaaaaaccat ttttgaacct taaaaggtac tggtactata
4201 gcattttgct atcttttta gtgttaagag ataaagaata ataattaacc aaccttgttt
4261 aatagatttg ggtcatttag aagcctgaca actcattttc atattgtaat ctatgtttat
4321 aatactacta ctgttatcag taatgctaaa tgtgtaataa tgtaacatga tttccctcca
4381 gagaaagcac aatttaaaac aatccttact aagtaggtga tgagtttgac agttttgac
4441 attttatatta aataacatgt ttctctataa agtatggtaa tagctttagt gaattaaatt
4501 tagttgagca tagagaacaa agtaaaagta gtgttgtcca ggaagtcaga attttaact
4561 gtactgaata ggttccccaa tccatcgtat taaaaaacaa ttaactgccc tctgaaataa
4621 tgggattaga aacaaacaaa actcttaagt cctaaaagtt ctcaatgtag aggcataaac
4681 ctgtgctgaa cataacttct catgtatatt acccaatgga aaatataatg atcagcaaaa
4741 agactggatt tgcagaagtt tttttttttt ttcttcatgc ctgatgaaag ctttggcaac
4801 cccaatatat gtattttttg aatctatgaa cctgaaaagg gtcagaagga tgcccagaca
4861 tcagcctcct tctttcaccc cttaccccaa agagaaagag tttgaaactc gagaccataa
4921 agatattctt tagtggaggc tggatgtgca ttagcctgga tcctcagttc tcaaatgtgt
4981 gtggcagcca ggatgactag atcctgggtt tccatccttg agattctgaa gtatgaagtc
5041 tgagggaaac cagagtctgt attttctaa actccctggc tgttctgatc ggccagtttt
5101 cggaaacact gacttaggtt tcaggaagtt gccatgggaa acaaataatt tgaactttgg
5161 aacagggttg gaattcaacc acgcaggaag cctactattt aaatccttgg cttcaggtta
5221 gtgacattta atgccatcta gctagcaatt gcgaccttaa tttaactttc cagtcttagc
5281 tgaggctgag aaagctaaag tttggttttg acaggttttc caaaagtaaa gatgctactt
5341 cccactgtat gggggagatt gaactttccc cgtctcccgt cttctgcctc ccactccata
5401 ccccgccaag gaaaggcatg tacaaaaatt atgcaattca gtgttccaag tctctgtgta
5461 accagctcag tgttttggtg gaaaaaacat tttaagtttt actgataatt tgaggttaga
5521 tgggaggatg aattgtcaca tctatccaca ctgtcaaaca ggttggtgtg ggttcattgg
5581 cattctttgc aatactgctt aattgctgat accatatgaa tgaaacatgg gctgtgatta
5641 ctgcaatcac tgtgctatcg gcagatgatg ctttggaaga tgcagaagca ataataaagt
5701 acttgactac ctactggtgt aatctcaatg caagcccaa cttcttatc caactttttc
5761 atagtaagtg cgaagactga gccagattga ccaattaaaa acgaaaacct gactaggttc
5821 tgtagagcca attagacttg aaatacgttt gtgtttctag aatcacagct caagcattct
5881 gtttatcgct cactctccct tgtacagcct tatttgttg gtgctttgca tttttgatatt
5941 gctgtgagcc ttgcatgaca tcatgaggcc ggatgaaact tctcagtcca gcagtttcca
6001 gtcctaacaa atgctcccac ctgaatttgt atatgactgc atttgtgggt gtgtgtgtgt
6061 tttcagcaaa ttccagattt gtttcctttt ggcctcctgc aaagtctcca gaagaaaatt
6121 tgccaatctt tcctactttc tattttatg atgacaatca aagccggcct gagaaacact
6181 atttgtgact ttttaaacga ttagtgatgt ccttaaaatg tggtctgcca atctgtacaa
6241 aatggtccta tttttgtgaa gagggacata agataaaatg atgttataca tcaatatgta
6301 tatatgtatt tctatataga cttggagaat actgccaaaa catttatgac aagctgtatc
6361 actgccttcg tttatattt tttaactgtg ataatcccca caggcacatt aactgttgca
6421 cttttgaatg tccaaaattt atatttaga aataataaaa agaaagatac ttacatgttc
6481 ccaaaacaat ggtgtggtga atgtgtgaga aaaactaact tgatagggtc taccaataca
6541 aaatgtatta cgaatgcccc tgttcatgtt tttgttttaa aacgtgtaaa tgaagatctt
6601 tatatttcaa taaatgatat ataatttaaa gtt
```

1. U87 Xenograft lysate
2. U87 Cell lysate
3. H358 Xenograft lysate
4. H358 cell lysate
5. U118 cell lysate Figure 5.
A.
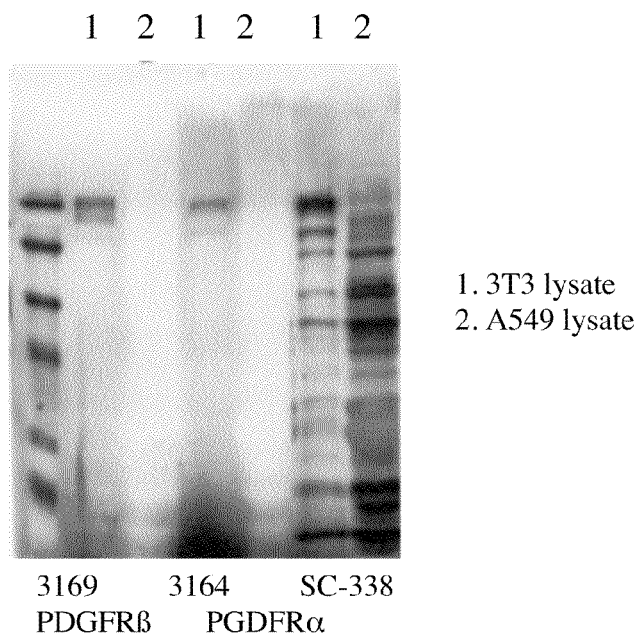
1. 3T3 lysate
2. A549 lysate
3169       3164      SC-338
PDGFRß    PGDFRα
B.
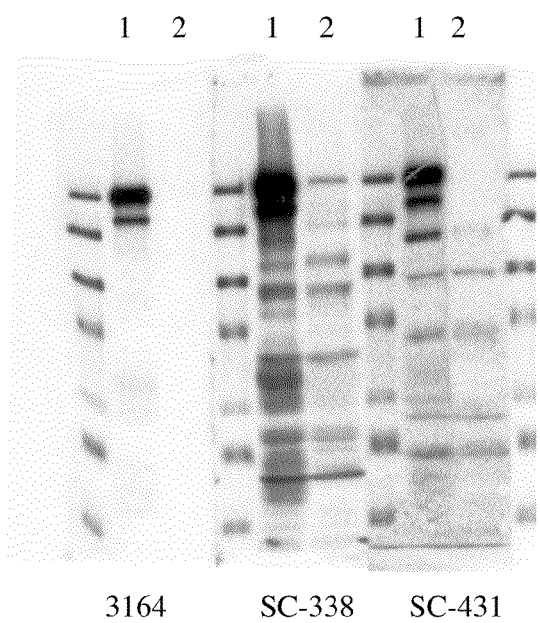
3164        SC-338      SC-431
1. H1703
2. A549

1. H1703/Unt
2. H1703/PDGFaa
3. A549/Unt
4. A549/PDGFaa

Figure 7. A549 xenograft IHC
SC-338
3164
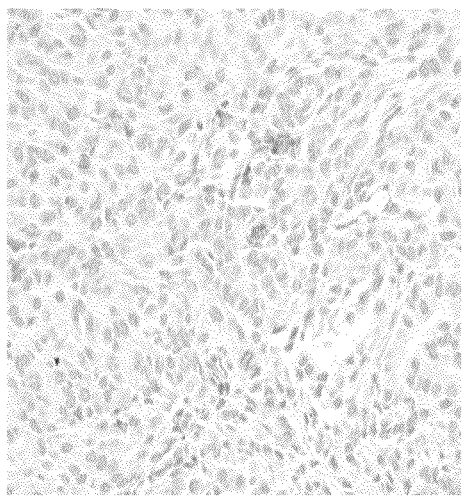
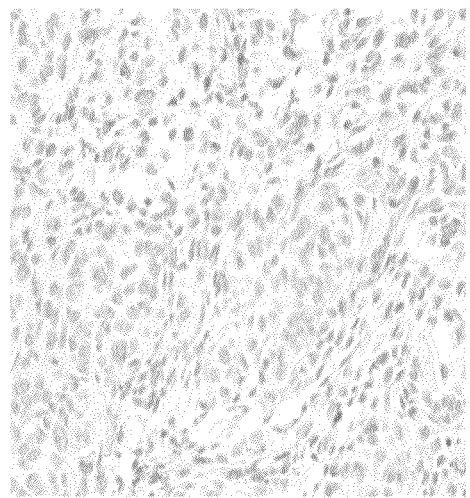

Figure 8.
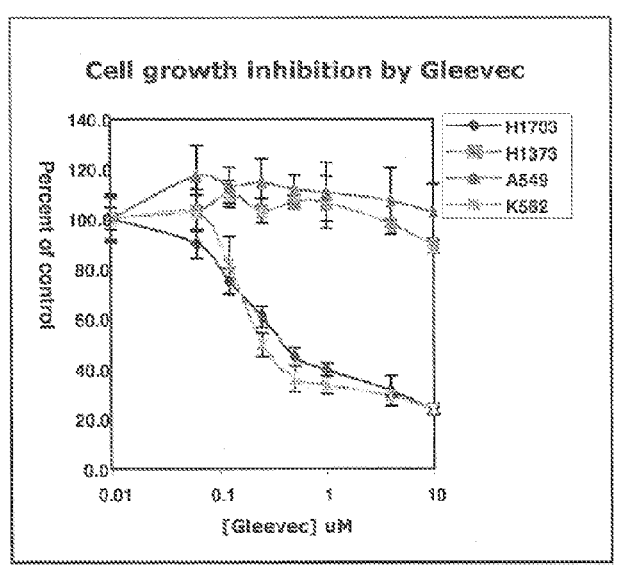
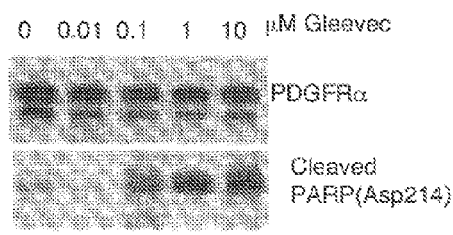
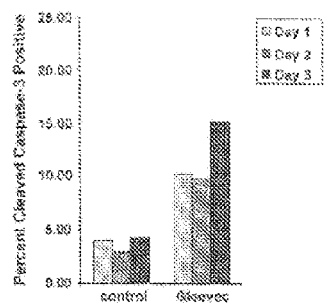

IDENTIFICATION OF NON-SMALL CELL LUNG CARCINOMA (NSCLC) TUMORS EXPRESSING PDGFR-ALPHA

This application is a divisional application of U.S. Ser. No. 11/174,051, filed on Jul. 1, 2005, issued as U.S. Pat. No. 7,932,044, the entire contents of which are hereby incorporated by reference.

FIELD OF THE INVENTION

The invention relates generally to cancer and antibodies, and the use of antibodies in characterizing cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the phosphorylation state, and thus the activity of, particular signaling proteins. Among these cancers is non-small cell lung carcinoma (NSCLC). NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. See "Cancer Facts and Figures 2003," American Cancer Society. NSCLC, which comprises three distinct subtypes, is often only detected after it has metastasized, and thus the mortality rate is 75% within two years of diagnosis.

NSCLC, like most cancers, involves defects in signal transduction pathways. Receptor tyrosine kinases (RTKs) play a pivotal role in these signaling pathways, transmitting extra-cellular molecular signals into the cytoplasm and/or nucleus of a cell. Among such RTKs are the receptors for polypeptide growth factors such as epidermal growth factor (EGF), insulin, platelet-derived growth factor (PDGF), neurotrophins (i.e., NGF), and fibroblast growth factor (FGF). Phosphorylation of such RTKs activates their cytoplasmic domain kinase function, which in turns activates downstream signaling molecules. Thus, RTKs are key mediators of cellular signaling as well as oncogenesis resulting from over-expression and activation of such RTKs and their substrates. Due to their pivotal role in normal and aberrant signaling, RTKs are the subject of increasing focus as potential drug targets for the treatment of certain types of cancer. For example, Herceptin®, an inhibitor of HER2/neu, is currently an approved therapy for a certain subset of breast cancer. Iressa™ (ZD1839) and Tarceva™ (OSI-774), both small-molecule inhibitors of EGFR, have been approved for the treatment of NSCLC.

Platelet-derived growth factor (PDGF) and its receptors (PDGFRs) are a family of RTKs that play an important role in the regulation of normal cell growth and differentiation. PDGFRs are involved in a variety of pathological processes, including atherosclerosis, neoplasia, tissue repair, and inflammation (see, e.g. Ross et al., Cell 46: 155-169 (1986); Ross et al., Adv. Exp Med. Biol. 234: 9-21 (1988)). PDGFRs, which consist of two isoforms (alpha ($\alpha$) and beta ($\beta$)), are membrane protein-tyrosine kinases that, upon binding to PDGF, become activated and, via recruitment of SH2 domain-containing effector molecules, initiate distinct or overlapping signaling cascades that coordinate cellular responses.

Expression of a constitutively active PDGFR leads to cellular transformation (see Gazit et al., Cell 39: 89-97 (1984)) and suggests that, in normal cells, PDGFR activity must be tightly regulated to oppose continuous activation of its downstream effectors. PDGFR beta, for example, is known to be over-expressed in a large number of tumors, and PDGF treatment causes transformation and malignant tumors in a variety of experimental systems (reviewed in Heldin et al., Physiol. Rev. 79(4): 1283-1316 (1999)). It has therefore been proposed that over-expression or constitutive activation of the PDGF receptors plays a role in the origin or tumorigenesis of certain cancer cells. It has been reported that PDGFR is activated by a fusion to the transcription factor TEL (see Ide et al., PNAS 99(22): 14404-14409 (2002)) in a subset of patients with chronic myelomonocytic leukemia (CML). PDGFR activation has also been implicated in growth of certain solid tumors, such as glioblastoma (see, e.g. Vassbotn et al., J. Cell. Physiol. 158: 381-389 (1994)).

Accordingly, inhibition of PDGFR and its downstream pathway has become an area of increasing focus for drug development. Specific inhibitors of PDGFR, such as the small-molecule drug Gleevec® (STI-571; Imatinib mesylate), have recently been developed and are in clinical trials for treatment of certain cancers, including prostate and ovarian cancers. It has been shown that Gleevec® induces durable responses in patients with chronic myelo-proliferative diseases associated with activation of PDGFR (see Apperley et al., N. Engl. J. Med 347(7): 481-7 (2002)). However, while PDGFR expression has been linked to the progression of a few cancers, such as CML and glioblastoma, this association has not been made in many other types of cancers. Similarly, although certain signaling defects underlying progression of NSCLC have been identified (including EGFR over-expression), the precise molecular mechanisms driving this disease are not completely understood.

One study reported the apparent expression of PDGFR alpha ($\alpha$) in nearly 100% of human lung cancer tumors examined, and reported the growth inhibition of a lung cancer cell line, A549, by Gleevec®, an effect that was surmised to be mediated via PDGFR inhibition (see Zhang et al., Mol. Cancer 2(1): 1-10 (2003)). The report, however, was inconclusive since the antibody employed in the study was later shown (by the present inventors) to be non-specific, and cross-reacts with a variety of proteins other than PDGFR$\alpha$; thus it is unclear which protein(s) was/were actually being detected in the Zhang study. Moreover, PDGFR$\alpha$ is not detectable in the A549 cell line employed in that study—which is consistent with the present inventors' inability to reproduce the growth inhibition of this cell line by Gleevec®—further evidencing that the observation reported in Zhang was either erroneous or was mediated by some mechanism other than expression and inhibition of PDGFR$\alpha$.

Since the new generation of targeted therapeutics against RTKs like PDGFR and EGFR are highly specific, there is a continuing and imperative need to identify the particular tumors that are, in fact, being driven by the RTK being targeted by these drugs, since such tumors are most likely to respond to the inhibitor. It is now widely accepted that most types of cancer have distinct subsets of tumors, which are being driven by different signaling pathways. For example, two distinct subsets of breast cancer are known to exist, one driven by Her2/Neu signaling and the other by EGFR signaling, but only the former is responsive to the Her2-targeted therapeutic Herceptin®. It is likely that most types of cancer, including those in which an RTK has already been identified (and targeted) as a driver of the disease, will in fact have multiple subtypes being driven by other, presently unknown RTKs and pathways. Indeed, the modest response rates thus far observed in clinical trials of several highly specific targeted therapeutics (including those against EGFR and PDGFR) evidence that many of the cancers being treated may, in fact, comprise subgroups being driven by alternative RTKs and pathways that are not being adequately targeted.

Accordingly, there is a continuing and pressing need to identify the particular signaling molecules, including RTKs, whose expression and/or activation is, in fact, driving a certain type of cancer (or a subset of that cancer). Identification of such signaling molecules will enable the development of new and improved diagnostic and/or prognostic assays to help ensure a particular patient gets a targeted therapeutic most likely to be effective against their disease, as well as providing novel drug targets for treatment of these cancers. Some cancers, like NSCLC, are often not detected until after the disease has already metastasized, making prompt and effective treatment paramount. Therefore, the ability to identify subgroups of cancers that are being driven by presently-untargeted RTKs and signaling pathways would greatly assist in developing alternative and more beneficial therapeutic strategies, and to avoiding prescribing ineffective therapies to patients who are not likely to respond to them.

SUMMARY OF THE INVENTION

In accordance with the invention, a previously unknown subset of mammalian non-small cell lung carcinoma (NSCLC) tumors in which platelet-derived growth factor receptor alpha (PDGFRα) is expressed, and driving the disease, has now been identified. The ability to identify NSCLC tumors in which PDGFRα is expressed and is driving the disease enables the identification of NSCLC tumors that are likely to respond to inhibitors of PDGFRα, such as Imatinib mesylate (STI-571; Gleevec®). The invention thus provides methods for identifying a mammalian NSCLC tumor that belongs to a subset of NSCLC tumors in which PDGFRα is expressed, and for identifying a NSCLC tumor that is likely to respond to a PDGFRα-inhibiting therapeutic. The invention also provides methods for determining whether a compound inhibits progression of a NSCLC tumor expressing PDGFRα, and for inhibiting the progression of a mammalian NSCLC tumor in which PDGFRα is expressed by inhibiting the activity of PDGFRα.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1—is the amino acid sequence (1-letter code) of human PDGFR alpha (α) (SEQ ID NO: 1) (SwissProt Accession No. P16234).

FIG. 3—is the DNA sequence encoding human PDGFRα (Accession No. NM_006206).

FIG. 5—consists of two Western blot analyses of extracts from three different cell lines using different anti-PDGFRα antibodies, demonstrating that some commercially available antibodies falsely detect PDGFRα in A549 cells.

FIG. 7—is an IHC analysis of H1703 xenograft samples probed with two antibodies made against PDGFRα. The results demonstrate that one of the commercial antibodies detects non-specific staining in the xenografts, consistent with the Western results on the cell lines.

FIG. 8—presents the effects of Gleevec® treatment on cell growth and cell apoptosis in NSCLC cell lines. Panel A presents growth curves for four cell lines with increasing concentrations of Gleevec® demonstrating that the H1703 cell line is sensitive to Gleevec®. Panel B presents Western blot results demonstrating that Gleevec® induces apoptosis in the H1703 cell line as shown by the cleavage of PARP. Panel C is a bar graph showing that apoptosis is induced in H1703 cells by administration of Gleevec®, as determined by presence of cleaved Caspase-3 using flow cytometry.

DETAILED DESCRIPTION OF THE INVENTION

Figure 2:
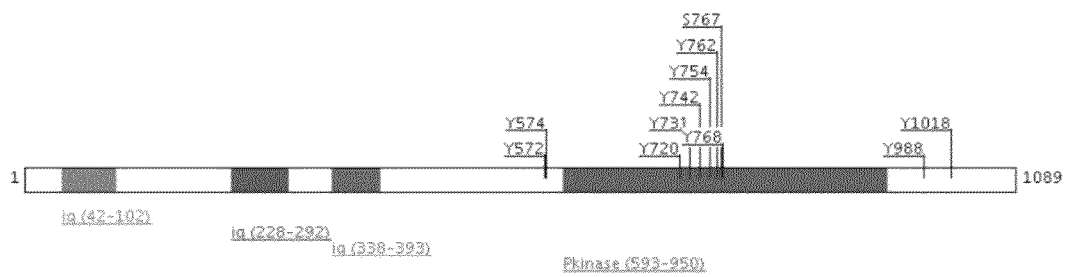
FIG. 2—is a graphic presentation of human PDGFRα kinase with the known/reported tyrosine phosphorylation sites labeled.

In accordance with the invention, a previously unknown subset of mammalian non-small cell lung carcinoma (NSCLC) tumors in which platelet-derived growth factor receptor alpha (PDGFRα) is expressed and is driving the disease has presently been identified. Epidermal growth factor receptor (EGFR) expression/activation is known to occur in many NSCLC tumors (see Neal et al., supra.; Sainsbury et al., supra.) and the receptor is presently a therapeutic target for the treatment of NSCLC. However, although activation of PDGFR is known to drive a subset of certain cancers, e.g. prostrate cancer, the association of PDGFRα expression in a subset of NSCLC tumors has not previously been conclusively reported.

A previous study (Zhang et al., supra.) reported the apparent expression of PDGFRα in nearly 100% of human lung cancer tumors examined. This study also reported that Gleevec® (STI-571), a small molecule inhibitor with activity against PDGFR, could inhibit the progression of a lung cancer cell line, A549, an effect that was thus surmised by the authors to be mediated via inhibition of PDGFRα in these cells. However, as presently shown (see Example 2), the possible antibodies employed in the study (obtained from Santa Cruz Biotechnology) are not specific for PDGFRα and in fact cross-react with a variety of other proteins. Accordingly, it is unclear which protein(s) was/were actually detected in the Zhang study and whether PDGFRα was expressed in the examined cells at all. Indeed, as presently shown (see Example 2), the A549 cell line employed in the Zhang study does not, in fact, express detectable PDGFRα. The lack of PDGFRα expression in this cell line is consistent with the present finding that Gleevec® does not, in fact, inhibit growth of this cell line, further evidencing that the observation reported in Zhang was either erroneous or was mediated by some mechanism other than PDGFRα inhibition.

The present discovery is surprising since a link between PDGFRα expression and a subset of NSCLC tumors has not, until now, been conclusively established, despite significant therapeutic development activity for this cancer. The identification of a distinct subset of NSCLC tumors in which PDGFRα is expressed has important implications for the management and treatment of this prevalent disease. NSCLC is the leading cause of cancer death in the United States, and is often difficult to diagnose until after it has metastatisized, increasing the difficulty of effectively treating or curing this disease. The mortality rate of NSCLC is therefore 75% within two years of diagnosis. See Amercian Cancer Society, supra. Although targeted EGFR-inhibitors are presently approved for the treatment of NSCLC, it is likely that this therapy will be ineffective against the subgroup of patients having tumors in which PDGFRα (rather than or in addition to EGFR) is expressed and driving the disease, in whole or in part.

The present discovery that a subset of NSCLC tumors is being driven by the expression of PDGFRα enables important new methods for accurately identifying mammalian NSCLC tumors in which PDGFRα is expressing, as these tumors are likely to respond to PDGFRα-inhibiting therapeutics, such as Imatinib mesylate (STI-571; Gleevec®). The ability to identify such tumors as early as possible will greatly assist in clinically determining which therapeutic, or combination of therapeutics, will be most appropriate for a particular NSCLC tumor, thus helping to avoid prescription of EGFR-inhibitors in cases where such inhibitors are likely to be partially or wholly ineffective (i.e. where receptors other than the one targeted are driving the disease, in whole or in part, in the tumor). Therefore, the invention provides, in part, methods for identifying a mammalian NSCLC tumor that belongs to a subset of NSCLC tumors in which PDGFRα is expressed. The identification of such a tumor identifies the tumor as being likely to respond to a composition comprising one or more PDGFRα-inhibiting therapeutics, such as Gleevec®.

The invention also provides a method for determining whether a compound inhibits the progression of a mammalian NSCLC tumor belonging to a subset of NSCLC tumors in which PDGFRα is expressed, by determining whether the compound inhibits the expression or activity of PDGFRα in such NSCLC tumor. Further provided by the invention is a method for inhibiting the progression of a mammalian NSCLC tumor in which PDGFRα is expressed by inhibiting the expression or activity of PDGFRα.

The further aspects, advantages, and embodiments of the invention are described in more detail below. All references cited herein are hereby incorporated by reference.

A. PDGFRα-Expressing Subset of NSCLC Tumors

A distinct subset of human NSCLC tumors in which PDGFRα is expressed and driving the disease was identified, surprisingly, during examination of global phosphorylated peptide profiles in extracts from known human NSCLC tumor cell lines including four cells lines; the A549, H441, H1373 and H1703 cell line. The phosphorylation profiles of these cell lines were elucidated using a recently described technique for the isolation and mass spectrometric characterization of modified peptides from complex mixtures (see U.S. Patent Publication No. 20030044848, Rush et al., "Immunoaffinity Isolation of Modified Peptides from Complex Mixtures" (the "IAP" technique), as further described in Example 1 herein. Application of the IAP technique using a phosphotyrosine-specific antibody (CELL SIGNALING TECHNOLOGY, INC., Beverly, Mass., 2003/04 Cat. #9411), identified that the H1703 cell expressed PDGFRα, in contrast to the other cell lines, which lacked PDGFRα but often expressed EGFR (Table 1, Example 1 lists the PDGFRα phosphosites only observed in the H1703 cell line). This novel finding indicated the existence of a previously unidentified subset of NSCLC tumors in which PDGFRα was expressed, and that this subset of tumors would likely survive despite clinically targeting only the EGFR pathway.

This initial finding was then confirmed by immunohistochemical (IHC) analysis of a tissue microarray comprising tumor biopsy tissue samples from 304 different human NSCLC patients, as further described in Example 3 below. Seventeen (17) out of 305 tumors (or 6% of all tumors examined) belonged to the PDGFRα-expressing subset, indicating that incidence of this subset of NSCLC tumors is rare (see Table 2 in Example 3). Within the PDGFRα-expressing subset of NSCLC tumors, adenocarcinomas and bronchioloalveolar carcinomas account for 76% (11 out of 17) of the tumors, and PGDFRα-expressing NSCLC tumors occur more often in women (65%, 11 out of 17) than in men.

The low frequency of PDGFRα-expressing NSCLC tumors (in the large patient sample population examined) disclosed herein starkly contrasts with the nearly 100% frequency reported in Zhang et al., supra., using a small (33 sample) patient population. This contrast indicates that the earlier report in Zhang was either erroneous, or resulted from the use of an antibody that was not in fact PDGFRα-specific, but rather binds multiple other proteins (see Example 2 below). Indeed, as presently shown (in Example 2), the A549 NSCLC cell line utilized in Zhang does not appreciably express PDGFRα and the growth of this cell line is not inhibited by the PDGFRα-inhibiting compound, Gleevec® (STI-571). See FIG. 10.

Figure 9:
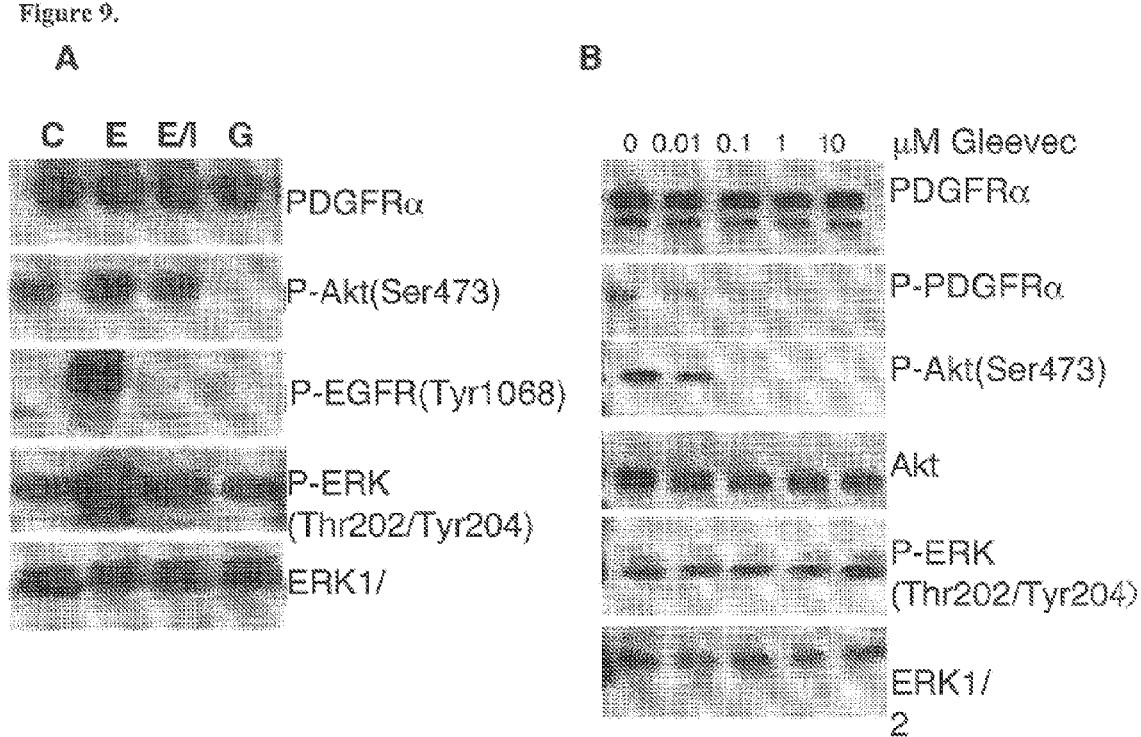
FIG. 9—is a Western blot analysis of extracts from H1703 cells treated with EGF, Gleevec® and Iressa®. The results demonstrate that the cell line has PDGFRα constitutively activated leading to AKT activation and that this activation may be inhibited by Gleevec® but not by Iressa®.
Figure 10:
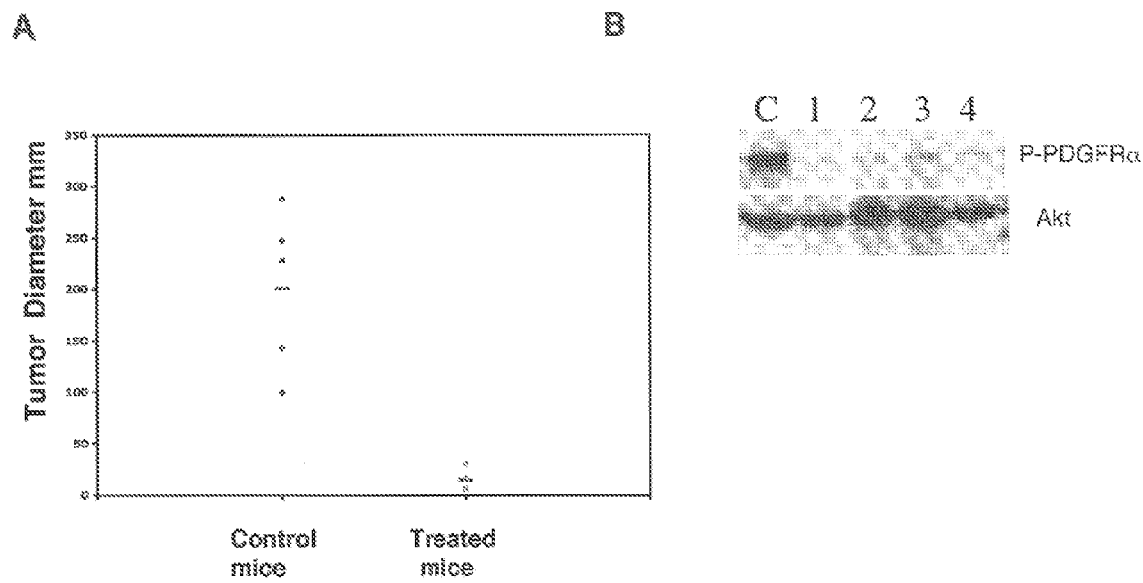
FIG. 10—depicts the inhibition of PDGFRα-expressing NSCLC tumor xenografts, in mice, by Gleevec®. Panel A is a graph showing reduction in tumor volume in mice treated with this PDGFRα inhibitor. Panel B is a Western blot analysis of tumor cell extracts from the mouse xenografts demonstrating that exposure of the xenograft to Gleevec® correlates with loss of PDGFRα phosphorylation, and no change in total AKT levels.

Inhibition of PDGFR activation and downstream signaling was then demonstrated on the H1703 cell line (see FIG. 9). In the same figure, results indicate that the constitutive cellular signal transduction in these cells is not affected by Iressa™ or EGFR inhibition. These results suggest that Gleevec treatment may inhibit tumor growth in tumors that are driven by PDGFRα. This hypothesis was tested using mouse xenografts derived from the H1703 cell line. Indeed, inhibition of PDGFRα activity in vivo was shown by treating mouse xenografts harboring PDGFRα-expressing human NSCLC tumors (H1703) with a small molecule targeted inhibitor of PDGFRα, Gleevec® (STI-571) as shown in FIGS. 9 and 10.

The ability to selectively identify NSCLC tumors that belong to a subset of NSCLC tumors in which PDGFRα is expressed and driving the disease (in whole or in part) enables important new methods for accurately identifying such tumors for diagnostic purposes, as well as obtaining information useful in determining whether such a tumor is likely to respond to a PDGFRα-inhibiting therapeutic composition, or likely to be partially or wholly non-responsive to an EGFR inhibitor when administered as a single agent for the treatment of NSCLC.

Accordingly, in one embodiment, the invention provides a method for identifying a mammalian non-small cell lung carcinoma (NSCLC) tumor that belongs to a subset of NSCLC tumors in which platelet-derived growth factor receptor alpha (PDGFRα) is expressed, said method comprising the step of determining whether PDGFRα is expressed in a biological sample comprising cells from a NSCLC tumor using at least one PDGFRα-specific reagent, wherein expression of PDGFRα in said biological sample identifies said NSCLC tumor as belonging to a subset of NSCLC tumors in which PDGFRα is expressed.

Biological samples useful in the practice of the present invention are described in further detail in section B below. In one preferred embodiment, the mammalian NSCLC tumor is a human tumor, while in other preferred embodiments the mammal is a dog, a cat, or a horse. In other preferred embodiments, the biological sample comprises cells (or lysates of cells) obtained from a tumor biopsy, a tumor fine needle aspirate, or a pleural effusion. In another preferred embodiment, identifying the NSCLC tumor as belonging to a subset of NSCLC tumors in which PDGFRα is expressed identifies the NSCLC tumor as being likely to respond to a composition comprising at least on PDGFRα-inhibiting therapeutic. PDGFRα-inhibiting therapeutics useful in the practice of the present invention is described in further detail in section F below. In one preferred embodiment, the PDGFRα-inhibiting therapeutic comprises a small molecule inhibitor of PDGFRα. In other preferred embodiments, the small molecule inhibitor of PDGFRα is Imatinib mesylate (STI-571; Gleevec®) or its analogues, while in another preferred embodiment, the small molecule inhibitor of PDGFRα is selected from the group consisting of BAY 43-93006, XL-999 and SU11248.

PDGFRα-specific reagents useful in the practice of the methods of the invention are described in further detail in section C below. In one preferred embodiment, the PDGFRα-specific reagent comprises a PDGFRα-specific antibody. Such antibody may, in one preferred embodiment, be a phosphorylation site-specific antibody. In another preferred embodiment, the PDGFRα-specific reagent comprises a heavy-isotope labeled phosphopeptide (AQUA peptide) corresponding to a PDGFRα peptide sequence (which may correspond to a phosphorylation site within PDGFRα).

The method of the invention described above may also optionally comprise the step of determining the level of activated or expressed epidermal growth factor receptor (EGFR) in said biological sample. Profiling both PDGFRα expression/activation and EGFR expression/activation in a given NSCLC tumor can provide valuable information on which pathway, or pathways, is/are driving the disease, and which therapeutic regime is therefore likely to be of most benefit.

The ability to identify a mammalian NSCLC tumor belonging to a subset of NSCLC tumors in which PDGFRα is activated can provide clinical information that is valuable to assessing whether a patient's tumor is likely to respond to a particular therapeutic (for example, an EGFR inhibitor or a PDGFRα inhibitor). Accordingly, in one preferred embodiment of the above-described method, identifying a NSCLC tumor as belonging to a subset of NSCLC tumors in which PDGFRα is activated identifies the tumor as likely to respond to a composition comprising at least one PDGFRα-inhibiting therapeutic. PDGFRα-inhibiting therapeutics useful in the practice of the methods of the invention is described in further detail in section E below.

PDGFRα-specific reagents, including antibodies and AQUA peptides, useful in the practice of the methods of the invention are described in further detail in section C below. In one preferred embodiment, the PDGFRα-specific reagent is an antibody, and in one preferred embodiment the antibody is a phosphorylation site-specific antibody that specifically binds PDGFRα only when phosphorylated. In another preferred embodiment, the PDGFRα-specific reagent is a heavy-isotope labeled phosphopeptide (AQUA peptide) corresponding to a PDGFRα peptide sequence.

The newly identified, distinct subset of mammalian NSCLC tumors in which PDGFRα is expressed and driving the disease (in whole or in part)—as opposed to the subset of tumors in which only EGFR is activated and driving the cancer—also has important implications for the treatment of NSCLC. The progression of NSCLC tumors belonging to the subset in which PDGFRα is driving the disease may be inhibited or stopped by inhibiting the expression and/or activity of PDGFRα (as opposed to targeting only EGFR, which is likely to be wholly or partially ineffective against this subset of tumors).

Accordingly, the invention also provides, in part, a method for inhibiting the progression of a mammalian NSCLC tumor belonging to a subset of NSCLC tumors in which PDGFRα is expressed, said method comprising the step of inhibiting the activity and/or expression of PDGFRα in the NSCLC tumor. In a preferred embodiment, the activity of PDGFRα is inhibited by contacting the tumor with a composition comprising at least one PDGFRα-inhibiting therapeutic. Compositions and PDGFRα-inhibiting compounds suitable for practice of the method of the invention are described in further detail in section E below. In one preferred embodiment, the PDGFRα-inhibiting therapeutic comprises a small molecule inhibitor of PDGFRα, and in some preferred embodiments, the small molecule inhibitor of PDGFRα is Imatinib mesylate (STI-571, Gleevec®) or its analogues. In other preferred embodiments, the small molecule inhibitor of PDGFRα is selected from the group consisting of BAY43-9006, XL-999 and SU11248. The NSCLC tumor may be contacted with a therapeutically effective amount of such PDGFRα-inhibiting therapeutic, in accordance with standard dosing and administration approaches.

The invention also provides, in part, a method for determining whether a compound inhibits the progression of a mammalian NSCLC tumor belonging to a subset of NSCLC tumors in which PDGFRα is expressed, the method comprising the step of determining whether the compound inhibits the expression and/or activity of PDGFRα in said NSCLC tumor. In one preferred embodiment, inhibition of activity of PDGFRα is determined by examining a biological sample comprising cells from said NSCLC tumor. In another preferred embodiment, inhibition of activity of PDGFRα is determined using at least one PDGFRα activation state-specific reagent, and in one preferred embodiment, the activation-state specific reagent is a phosphorylation-site specific antibody. The compound may, for example, be a kinase inhibitor, such as a small molecule or antibody inhibitor. PDGFRα-inhibiting compounds are discussed in further detail in section E below. Patient biological samples may be taken before and after treatment with the inhibitor and then analyzed, using methods described below in section D, for the biological effect of the inhibitor on PDGFRα phosphorylation or the phosphorylation of downstream proteins. Such a pharmacodynamic assay may be useful in determining the biologically active dose of the drug which may be preferable to a maximal tolerable dose. Such information would also be useful in submissions for drug approval by demonstrating the mechanism of drug action.

Definitions.

As used throughout this specification, the following terms have the meanings indicated:

"cells from a NSCLC tumor" means whole cells or extracts of cells from a NSCLC tumor or neoplasm.

"expression" or "expressed" with respect to PDGFRα in a biological sample means significantly expressed as compared to control sample in which PDGFRα is not significantly expressed.

"PDGFRα-specific reagent" means any detectable reagent, chemical or biological, which can specifically react with, bind to, detect, and/or quantify PDGFRα in a biological sample, and which does not substantially react with PDGFR beta (β) or other RTKs or kinases, as compared to the reagent's reactivity to PDGFRα.

"PDGFRα-inhibiting therapeutic" means any composition comprising one or more compounds, chemical or biological, which inhibits, either directly or indirectly, the expression and/or activity of PDGFRα in vivo.

B. Biological Samples

Biological samples useful in the practice of the methods of the invention may be obtained from any mammal in which a NSCLC tumor is present or developing. In one embodiment, the mammal is a human, and the human may be a candidate for a PDGFRα-inhibiting therapeutic, for the treatment of NSCLC. The human candidate may be a patient currently being treated with, or considered for treatment with, an EGFR inhibitor, such as Tarceva™ or Iressa™. In another embodiment, the mammal is large animal, such as a horse or cow, while in other embodiments, the mammal is a small animal, such as a dog or cat, all of which are known to develop NSCLC.

Any biological sample comprising cells (or extracts of cells) from a mammalian NSCLC tumor is suitable for use in the methods of the invention. In one embodiment, the biological sample comprises cells obtained from a tumor biopsy. The biopsy may be obtained, according to standard clinical techniques, from primary NSCLC tumors occurring in the lung of a mammal, or by secondary NSCLC tumors that have metastasized in other tissues. In another embodiment, the biological sample comprises cells obtained from a fine needle aspirate taken from a NSCLC tumor, and techniques for obtaining such aspirates are well known in the art (see Cristallini et al., *Acta Cytol.* 36(3): 416-22 (1992))

In still another preferred embodiment, the biological sample comprises cells obtained from a NSCLC pleural effusion. Pleural effusions (liquid that forms outside the lung in the thoracic cavity and which contains cancerous cells) are known to form in many patients with advanced NSCLC, and the presence of such effusion is predictive of a poor outcome and short survival time. See Mott et al., *Chest* 119: 317-318 (2001). Effective and prompt treatment is therefore particularly critical in such cases. Standard techniques for obtaining pleural effusion samples have been described and are well known in the art (see Sahn *Clin Chest Med.* 3(2): 443-52 (1982)). Circulating NSCLC cells may also be obtained from serum using tumor markers, cytokeratin protein markers or other methods of negative selection as described (see Ma et al. *Anticancer Res.* 23(1A): 49-62 (2003)).

A biological sample may comprise cells from a NSCLC tumor in which PDGFRα is expressed and activated but EGFR is not. Alternatively, the sample may comprise cells from a NSCLC tumor in which both PDGFRα and EGFRα are expressed and activated, or in which EGFRα is expressed and activated but PDGFRα is not.

Cellular extracts of the foregoing biological samples may be prepared, either crude or partially (or entirely) purified, in accordance with standard techniques, and used in the methods of the invention. Alternatively, biological samples comprising whole cells may be utilized in preferred assay formats such as immunohistochemistry (IHC), flow cytometry (FC), and immunofluorescence (IF), as further described in section D below. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In practicing the disclosed method for determining whether a compound inhibits progression of a NSCLC tumor in which PDGFRα is expressed, biological samples comprising cells from mammalian xenografts may also be advantageously employed. Preferred xenografts are small mammals, such as mice, harboring human NSCLC tumors that express PDGFRα. Xenografts harboring human NSCLC tumors are well known in the art (see Kal, *Cancer Treat Res.* 72: 155-69 (1995)) and the production of mammalian xenografts harboring human tumors is well described (see Winograd et al., In Vivo. 1(1): 1-13 (1987)).

In assessing PDGFRα expression in a biological sample comprising cells from a mammalian NSCLC tumor, a control sample representing the background in vivo activation of PDGFRα may desirably be employed for comparative purposes. Ideally, the control sample comprises cells from a NSCLC tumor that is representative of the subset of NSCLC tumors in which PDGFRα is not expressed. Comparing the level of expressed PDGFRα in control sample versus the test biological sample thus identifies whether PDGFRα is expressed. Alternatively, since PDGFRα is not expressed in the majority of NSCLC tumors (that do not belong to the presently disclosed subset of tumors), any tissue that similarly does not express PDGFRα may be employed as a control.

The methods described above will have valuable diagnostic utility for mammalian NSCLC tumors, and treatment decisions pertaining to the same. For example, biological samples may be obtained from a subject that has not been previously diagnosed as having NSCLC, nor has yet undergone treatment for such cancer, and the method is employed to diagnostically identify a NSCLC tumor in such subject as belonging to a subset of NSCLC tumors in which PDGFRα is expressed. Alternatively, a biological sample may be obtained from a subject that has been diagnosed as having NSCLC and has been receiving therapy, such as EGFR inhibitor therapy (e.g. Tarceva™, Iressa™) for treatment of such cancer, and the method of the invention is employed to identify whether the subject's NSCLC tumor belongs to a subset of NSCLC that is likely to respond to such therapy and/or whether alternative or additional PDGFRα-inhibiting therapy is desirable or warranted. The methods of the invention may also be employed to monitor the progression or inhibition of a PDGFRα-expressing NSCLC tumor following treatment of a subject with a composition comprising a PDGFRα-inhibiting therapeutic or combination of therapeutics.

Such diagnostic assay may be carried out subsequent to or prior to preliminary evaluation or surgical surveillance procedures. The identification method of the invention may be advantageously employed as a diagnostic to identify NSCLC patients having tumors driven by PDGFRα, which patients would be most likely to respond to therapeutics targeted at inhibiting PDGFRα activity, such as STI-571 (Gleevec®) or its analogues. The ability to select such patients would also be useful in the clinical evaluation of efficacy of future PDG- FRα-targeted therapeutics as well as in the future prescription of such drugs to NSCLC patients.

C. PDGFRα-Specific Reagents

PDGFRα-activation state-specific reagents useful in the practice of the disclosed methods include, among others, PDGFRα-specific antibodies and AQUA peptides (heavy-isotope labeled peptides) corresponding to, and suitable for detection and quantification of, PDGFRα expression in a biological sample. A PDGFRα-specific reagent is any reagent, biological or chemical, capable of specifically binding to, detecting and/or quantifying the presence/level of expressed PDGFRα in a biological sample. The term includes, but is not limited to, the preferred antibody and AQUA peptide reagents discussed below, and equivalent reagents are within the scope of the present invention.

Antibodies.

Antibodies suitable for use in practice of the methods of the invention include a PDGFRα-specific antibody and a PDGFRα phosphorylation site-specific antibody. A PDGFRα-specific antibody is an isolated antibody or antibodies that specifically bind(s) the PDGFR alpha (α) protein (e.g. human, see SEQ ID NO: 1) regardless of phosphorylation state, but including phosphorylated forms of the protein. A PDGFRα phosphorylation site-specific antibody is an isolated antibody or antibodies that specifically bind(s) PDGFR alpha (α) protein only when phosphorylated at a particular tyrosine, serine, or threonine residue, and does not substantially bind the unphosphorylated form of the protein, or the protein when phosphorylated at a different site than that for which the antibody is specific.

Human PDGFRα-specific, and phosphorylation site-specific, antibodies may also bind to highly homologous and equivalent epitopic peptide sequences in other mammalian species, for example murine or rabbit PDGFRα, and vice versa. Antibodies useful in practicing the methods of the invention include (a) monoclonal antibodies, (b) purified polyclonal antibodies that specifically bind to the target protein (e.g. a phosphorylated form of PDGFRα), (c) antibodies as described in (a)-(c) above that bind equivalent and highly homologous epitopes or phosphorylation sites in other non-human species (e.g. mouse, rat), and (d) fragments of (a)-(c) above that bind to the antigen (or more preferably the epitope) bound by the exemplary antibodies disclosed herein.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.)

PDGFRα-specific antibodies are commercially available (see Cell Signaling Technology, 2005 Catalogue, #3164, and Santa Cruz Biotechnology, 2005 Catalogue, #338). Certain preferred embodiments of the methods of the invention employ a phosphorylation site-specific antibody that specifically binds PDGFRα only when phosphorylated at a tyrosine known to be relevant to protein activity, for example tyrosines 720 and 754 in the human PDGFRα protein sequence (SEQ ID NO: 1). Some or all of these phosphorylation-site specific antibodies are commercially available (see Cell Signaling Technology 2005 Catalogue, #2992, and Santa Cruz Biotechnology, 2005 Catalogue, #12911). The production and use of PDGFRα-specific antibodies has been described. See, e.g. U.S. Pat. No. 6,660,488, Dec. 9, 2003, Matsui et al.

The preferred epitopic site of a PDGFRα-specific antibody of the invention is a peptide fragment consisting essentially of about 11 to 17 amino acids of the human PDGFRα protein sequence (SEQ ID NO: 1). For PDGFRα phosphorylation site-specific antibodies, the epitope comprises the particular phosphorylated residue (tyrosine, serine, or threonine), with about 5 to 9 amino acids positioned on each side of it (for example, residues 746-762 of SEQ ID NO: 1, comprising the phosphotyrosine at position 754). It will be appreciated that antibodies that specifically binding shorter or longer peptides/epitopes within PDGFRα are within the scope of the present invention. The amino acid sequence of human PDGFRα has been published (see FIG. 1 (SEQ ID NO: 1), as are the sequences of PDGFRα from other species.

The invention is not limited to use of antibodies, but includes equivalent molecules, such as protein binding domains or nucleic acid aptamers, which bind, in a fusion-protein specific manner, to essentially the same epitope to which a PDGFRα antibody useful in the methods of the invention binds. See, e.g., Neuberger et al., *Nature* 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired epitope of PDGFRα, collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of assay methods provided by the invention. For example, a solution containing the appropriate antigen (e.g. a synthetic peptide comprising a phosphorylation site within PDGFRα) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below.

The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods,* 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Antibodies useful in the methods of the invention, whether polyclonal or monoclonal, may be screened for epitope and phosphorylation-state specificity according to standard techniques. See, e.g. Czernik et al., *Methods in Enzymology,* 201: 264-283 (1991). For example, the antibodies may be screened against a peptide library by ELISA to ensure specificity for both the desired antigen and, if desired, for reactivity only with the phosphorylated form of the antigen. The antibodies may also be tested by Western blotting against cell preparations containing target protein to confirm reactivity with the only the desired target and to ensure no appreciable binding to other isoforms of PDGFR.

PDGFRα-specific, and phosphorylation-specific, antibodies useful in the methods of the invention may exhibit some limited cross-reactivity with non-PDGFRα epitopes. This is not unexpected as most antibodies exhibit some degree of cross-reactivity, and anti-peptide antibodies will often cross-react with epitopes having high homology or identity to the immunizing peptide. See, e.g., Czernik, supra. Cross-reactivity with non-PDGFRα proteins is readily characterized by Western blotting alongside markers of known molecular weight. Amino acid sequences of cross-reacting proteins may be examined to identify sites highly homologous or identical to the PDGFRα sequence to which the antibody binds. Undesirable cross-reactivity can be removed by negative selection using antibody purification on peptide columns.

PDGFRα-specific antibodies useful in practicing the methods of the invention are ideally specific for human PDGFRα, but are not limited only to binding the human species, per se. The invention includes the use of antibodies that also bind conserved and highly homologous or identical epitopes in other mammalian species (e.g. mouse, rat, monkey). Highly homologous or identical sequences in other species can readily be identified by standard sequence comparisons, such as using BLAST, with the human PDGFRα sequence disclosed herein (SEQ ID NO: 1).

Antibodies employed in the methods of the invention may be further characterized by, and validated for, use in a particular assay format, for example FC, IHC, and/or ICC. The use of antibodies against PDGFRα in such methods is further described in section D below. Antibodies may also be advantageously conjugated to fluorescent dyes (e.g. Alexa488, PE), or labels such as quantum dots, for use in multi-parametric analyses along with other signal transduction (phospho-AKT, phospho-Erk 1/2) and/or cell marker (cytokeratin) antibodies, as further described in section D below.

In practicing the methods of the invention, the expression and/or activity of EGFR in a given NSCLC tumor may also be advantageously examined using an EGFR-specific antibody and/or an EGFR phosphorylation site-specific antibody. EGFR-specific and phosphorylation-site specific antibodies are commercially available (see CELL SIGNALING TECHNOLOGY, INC., Beverly Mass., 2003/04 Catalogue, #'s 2231, 2232, and 2234-2237; and Santa Cruz Biotechnology, 2005 Catalogue, #03). Such antibodies may also be produced according to standard methods, as described above. The amino acid sequence of human EGFR is published (see accession #NP-005219), as are the sequences of EGFR from other species. Detection of EGFR expression and/or activation, along with PDGFRα expression, in an NSCLC tumor can provide information on whether PDGFRα alone is driving the tumor, or whether EGFR is also activated and driving the tumor. Such information is clinically useful in assessing whether targeting either, or both, receptors is likely to be most beneficial in inhibiting progression of the NSCLC tumor, and in selecting an appropriate therapeutic or combination thereof.

It will be understood that more than one antibody may be used in the practice of the above-described methods. For example, one or more PDGFRα-specific antibodies together with one or more antibodies specific for another kinase, receptor, or kinase substrate that is suspected of being, or potentially is, activated in a NSCLC tumor may be simultaneously employed to detect the activity of such other signaling molecules in a biological sample comprising cells from such NSCLC tumor.

Heavy-Isotope Labeled Peptides (AQUA Peptides).

PDGFRα-activation state-specific reagents useful in the practice of the disclosed method may also comprise heavy-isotope labeled peptides suitable for the absolute quantification of expressed PDGFRα (preferably phosphorylated at a disclosed site) in a biological sample. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known phosphorylation site sequence previously identified by the IAP-LC-MS/MS method within in a target protein. One AQUA peptide incorporating the phosphorylated form of the particular residue within the site may be developed, and a second AQUA peptide incorporating the non-phosphorylated form of the residue developed. In this way, the two standards may be used to detect and quantify both the phosphorylated and non-phosphorylated forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and MS³ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or MS″ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may desirably be produced, as described above, to detect any quantify any phosphorylation site with PDGFRα relevant to activity of this RTK. For example, an AQUA phosphopeptide may be prepared that corresponds to any of the following preferred PDGFRα tyrosine phosphorylation sites: tyrosine 572, tyrosine 742, tyrosine 762, tyrosine 768, tyrosine 849, or tyrosine 1018 (in the human PDGFRα protein sequence (SEQ ID NO: 1); see also Table 1). Peptide standards for a given phosphorylation site (e.g. the tyrosine 572 site in human PDGFRα) may be produced for both the phosphorylated and non-phosphorylated forms of the site, and such standards employed in the AQUA methodology to detect and quantify both forms of such phosphorylation site in a biological sample.

The six phosphorylation site peptide sequences identified in Table 1 (see Example 1) (SEQ ID NOs: 3-8) are particularly well suited for development of corresponding AQUA peptides, since the IAP method by which they were identified (see Part A above, and Example 1) inherently confirmed that such peptides are in fact produced by enzymatic digestion (trypsinization) and are in fact suitably fractionated/ionized in MS/MS. For example, the peptide sequence QADT-TQyVPMLER (SEQ ID NO: 4; see Table 1), which encompasses phosphorylatable tyrosine 742 (human PDGFRα sequence) may desirably be selected for development of AQUA peptides for quantifying phosphorylated (Y742) PDGFRα in a biological sample. Heavy-isotope labeled equivalents of any of these preferred peptides (both in phosphorylated and unphosphorylated form) can be readily synthesized and their unique MS and LC-SRM signature determined, so that the peptides are validated as AQUA peptides and ready for use in quantification experiments.

It will be appreciated that larger AQUA peptides comprising a PDGFRα phosphorylation site sequence (and additional residues downstream or upstream of it) may also be constructed. Similarly, a smaller AQUA peptide comprising less than all of the residues of such phosphorylation site sequence (but still comprising the phosphorylatable tyrosine residue of interest) may alternatively be constructed. Such larger or shorter AQUA peptides are within the scope of the present invention, and the selection and production of preferred AQUA peptides, whether to quantify total PDGFRα or phosphorylated PDGFRα, may be carried out as described above (see Gygi et al., Gerber et al., supra.).

D. Assay Formats

Immunoassays useful in the practice of the methods of the invention may be homogenous immunoassays or heterogeneous immunoassays. In a homogeneous assay the immunological reaction usually involves a PDGFRα-specific reagent (e.g. a PDGFRα-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semi-conductor nanocrystal labels, or "quantum dots", may also be advantageously employed, and their preparation and use has been well described. See generally, K. Barovsky, Nanotech. Law & Bus. 1(2): Article 14 (2004) and patents cited therein.

In a heterogeneous assay approach, the reagents are usually the biological sample, a PDGFRα-specific reagent (e.g., an antibody), and suitable means for producing a detectable signal. Biological samples as described above in section B may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. PDGFRα-specific or phosphorylation site-specific monoclonal antibodies may be used in a "two-site" or "sandwich"

assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of PDGFRα is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other PDGFRα binding reagents may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), or immunofluorescence (IF) are particularly desirable in practicing the methods of the invention, since such assay formats are clinically-suitable, allow the detection of PDGFRα activation in vivo, and avoid the risk of artifact changes in activity resulting from manipulating cells obtained from an NSCLC tumor in order to obtain extracts. Accordingly, in some preferred embodiment, the methods of the invention are implemented in a flow-cytometry (FC), immuno-histochemistry (IHC), or immunofluorescence (IF) assay format.

Flow cytometry (FC) may be employed to determine the activation status of PDGFRα in a mammalian NSCLC tumor before, during, and after treatment with a drug targeted at inhibiting PDGFRα kinase activity. For example, tumor cells from a fine needle aspirate may be analyzed by flow cytometry for PDGFRα expression and/or activation, as well as for markers identifying lung cancer cell types, etc., if so desired. Flow cytometry may be carried out according to standard methods. See, e.g. Chow et al., Cytometry (*Communications in Clinical Cytometry*) 46: 72-78 (2001). Briefly and by way of example, the following protocol for cytometric analysis may be employed: fixation of the cells with 2% paraformaldehyde for 10 minutes at 37° C. followed by permeabilization in 90% methanol for 30 minutes on ice. Cells may then be stained with the primary PDGFRα-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed PDGFRα protein in the tumor. Similar analysis after treatment of the tumor with a PDGFRα-inhibiting therapeutic would reveal the responsiveness of a PDGFRα-expressing tumor to the targeted inhibitor or PDGFRα kinase.

Immunohistochemical (IHC) staining may be also employed to determine the expression and/or activation status of PDGFRα in a mammalian NSCLC tumor before, during, and after treatment with a drug targeted at inhibiting PDGFRα activity. IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-PDGFRα antibody and secondary antibody; and finally detecting using ABC avidin/biotin method according to manufacturer's instructions.

Immunofluorescence (IF) assays may be also employed to determine the expression and/or activation status of PDGFRα in a mammalian NSCLC tumor before, during, and after treatment with a drug targeted at inhibiting PDGFRα kinase activity. IF may be carried out according to well-known techniques. See, e.g., J. M. polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody against PDGFRα followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (EGFR, phospho-AKT, phospho-Erk 1/2) and/or cell marker (cytokeratin) antibodies.

Similarly, AQUA peptides for the detection/quantification of expressed PDGFRα in a biological sample comprising cells from a NSCLC tumor may be prepared and used in standard AQUA assays, as described in detail in section C above. Accordingly, in some preferred embodiments of the methods of the invention, the PDGFRα-specific reagent comprises a heavy isotope labeled phosphopeptide (AQUA peptide) corresponding to a PDGFRα peptide sequence (e.g., a phosphorylation site), as described above in section C.

PDGFRα-specific reagents useful in practicing the methods of the invention may also be mRNA, oligonucleotide or DNA probes that can directly hybridize to, and detect, PDGFRα expression transcripts in a biological sample. Briefly, and by way of example, formalin-fixed, paraffin-embedded patient samples may be probed with a fluorescein-labeled RNA probe followed by washes with formamide, SSC and PBS and analysis with a fluorescent microscope.

E. PDGFRα-Inhibiting Therapeutics

In accordance with the present invention, it has now been shown that the progression of a distinct subset of mammalian NSCLC tumors in which PDGFRα is expressed may be inhibited, in vivo, by inhibiting the activity of PDGFRα in such tumors. PDGFRα activity in this newly identified and distinct subset of NSCLC tumors may be inhibited by contacting the tumor with a PDGFRα-inhibiting therapeutic, such as a small-molecule PDGFRα inhibitor like Imatinib mesylate (STI-571; Gleevec®). As further described in Example 5 herein, growth inhibition of PDGFRα-expressing NSCLC tumors can be accomplished by inhibiting this RTK, using an exemplary PDGFRα-inhibiting therapeutic, Gleevec®. Accordingly, the invention provides, in part, a method for inhibiting the progression of a PDGFRα-expressing mammalian NSCLC tumor by inhibiting the expression and/or activity of PDGFRα in the tumor.

A PDGFR-inhibiting therapeutic may be any composition comprising at least one compound, biological or chemical, which inhibits, directly or indirectly, the expression and/or activity of PDGFRα in vivo, including the exemplary classes of compounds described below. Such compounds include therapeutics that act directly on PDGFRα itself, or on proteins or molecules that modify the activity of PDGFRα, or that act indirectly by inhibiting the expression of PDGFRα. Such compositions also include compositions comprising only a single PDGFRα-inhibiting compound, as well as compositions comprising multiple therapeutics (including those against other RTKs), which may also include a non-specific therapeutic agent like a chemotherapeutic agent or general transcription inhibitor.

Small-Molecule Inhibitors.

In some preferred embodiments, a PDGFRα-inhibiting therapeutic useful in the practice of the methods of the invention is a targeted, small molecule inhibitor, such as Gleevec® (STI-571), and its analogues. As presently shown (see Example 5), administration of Gleevec® to mice harboring human NSCLC xenografts selectively inhibited the progression of the disease in those mice with PDGFRα-expressing tumors. Gleevec®, which specifically binds to and blocks the ATP-binding site of PDGFRα (as well as Bcr-Abl kinase), thereby preventing phosphorylation and activation of this enzyme, is commercially available and its properties are well known. The PDGFRα-specific inhibitory properties of Gleevec® have been described. See, e.g. Martinelli et al., *Haematologica* 89(2): 236-7 (2004). Other preferred small-molecule inhibitors of PDGFR include BAY 43-93006, XL-999 and SU11248. These compounds are under clinical investigation and their PDGFRα-specific inhibitory properties have been described. See Wilhelm et al., *Cancer Res.* 64(19): 7099-109 (2004) and Mendel et al., *Clin Cancer Res.* 9(1): 327-37 (2003).

Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity. Small molecule inhibitors may be rationally designed using X-ray crystallographic or computer modeling of PDGFRα three-dimensional structure, or may found by high throughput screening of compound libraries for inhibition of PDGFRα. Such methods are well known in the art, and have been described. Specificity of PDGFRα inhibition may be confirmed, for example, by examining the ability of such compound to inhibit PDGFRα activity, but not other kinase activity, in a panel of kinases, and/or by examining the inhibition of PDGFRα activity in a biological sample comprising NSCLC tumor cells, as described above. Such screening methods are further described below.

Other small molecules with PDGFRα-inhibitory properties, such as quinoline and quinoxaline compounds, and 1,3-diazine compounds, have been described. See, e.g. U.S. Pat. Nos. 6,821,962; 6,696,434; 6,169,088. Methods for identifying antagonists of PDGFRα have also been described. See, e.g. U.S. Pat. No. 6,566,075, May 20, 2003, Escobedo et al.

Antibody Inhibitors.

PDGFRα-inhibiting therapeutics useful in the methods of the invention may also be targeted antibodies that specifically bind to critical catalytic or binding sites or domains required for PDGFRα activity, and inhibit the kinase by blocking access of substrates or secondary molecules to PDGFRα and/or preventing the enzyme from adopting a conformation necessary for its activity. The production, screening, and therapeutic use of humanized target-specific antibodies has been well-described. See Merluzzi et al., *Adv Clin Path.* 4(2): 77-85 (2000).

Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, "Antibodies to IGF-I Receptor for the Treatment of Cancers," Oct. 14, 2004, Morton et al.; U.S. Patent Publication No. 20040086503, "Human anti-Epidermal Growth Factor Receptor Single-Chain Antibodies," Apr. 15, 2004, Raisch et al.; U.S. Patent Publication No. 20040033543, "Treatment of Renal Carcinoma Using Antibodies Against the EGFr," Feb. 19, 2004, Schwab et. al. Standardized methods for producing, and using, receptor tyrosine kinase activity-inhibiting antibodies are known in the art. See, e.g., European Patent No. EP1423428, "Antibodies that Block Receptor Tyrosine Kinase Activation, Methods of Screening for and Uses Thereof," Jun. 2, 2004, Borges et al.

Phage display approaches may also be employed to generate PDGFRα-specific antibody inhibitors, and protocols for bacteriophage library construction and selection of recombinant antibodies are provided in the well-known reference text CURRENT PROTOCOLS IN IMMUNOLOGY, Colligan et al. (Eds.), John Wiley & Sons, Inc. (1992-2000), Chapter 17, Section 17.1. See also U.S. Pat. No. 6,319,690, Nov. 20, 2001, Little et al.; U.S. Pat. No. 6,300,064, Oct. 9, 2001, Knappik et al.; U.S. Pat. No. 5,840,479, Nov. 24, 1998, Little et al.; U.S. Patent Publication No. 20030219839, Nov. 27, 2003, Bowdish et al.

A library of antibody fragments displayed on the surface of bacteriophages may be produced (see, e.g. U.S. Pat. No. 6,300,064, Oct. 9, 2001, Knappik et al.) and screened for binding to a soluble dimeric form of a receptor protein tyrosine kinase. An antibody fragment that binds to the soluble dimeric form of the RTK used for screening is identified as a candidate molecule for blocking constitutive activation of the target RTK in a cell. See European Patent No. EP1423428, Borges et al., supra.

PDGFRα-binding targeted antibodies identified in screening of antibody libraries as describe above may then be further screened for their ability to block the activity of PDGFRα, both in vitro kinase assay and in vivo in cell lines and/or tumors. PDGFRα inhibition may be confirmed, for example, by examining the ability of such antibody therapeutic to inhibit PDGFRα activity, but not other kinase activity, in a panel of kinases, and/or by examining the inhibition of PDGFRα activity in a biological sample comprising NSCLC tumor cells, as described above. Methods for screening such compounds for PDGFRα inhibition are further described above.

Indirect Inhibitors.

PDGFRα-inhibiting compounds useful in the practice of the disclosed methods may also be compounds that indirectly inhibit PDGFRα activity by inhibiting the activity of proteins or molecules other than PDGFRα itself. Such inhibiting therapeutics may be targeted inhibitors that modulate the activity of key regulatory kinases that phosphorylate or de-phosphorylate (and hence activate or deactivate) PDGFRα itself. As with other receptor tyrosine kinases, PDGFRα regulates downstream signaling through a network of adaptor proteins and downstream kinases. As a result, induction of cell growth and survival by PDGFRα activity may be inhibited by targeting these interacting or downstream proteins. Drugs currently in development that could be used in this manner include AKT inhibitors (RX-0201) and mTOR inhibitors (rapamycin and its analogs such as CC1-779, Rapamune and RAD001).

PDGFRα activity may also be indirectly inhibited by using a compound that inhibits the binding of an activating molecule, such as the platelet-derived growth factor (PDGF) A or B, necessary for PDGFRα to adopt its active conformation. For example, the production and use of anti-PDGF antibodies has been described. See U.S. Patent Publication No.

20030219839, "Anti-PDGF Antibodies and Methods for Producing Engineered Antibodies," Bowdish et al. Inhibition of PDGF binding to PDGFRα directly down-regulates PDGFRα activity.

Indirect inhibitors of PDGFRα activity may be rationally designed using X-ray crystallographic or computer modeling of PDGFRα three dimensional structure, or may found by high throughput screening of compound libraries for inhibition of key upstream regulatory enzymes and/or necessary binding molecules, which results in inhibition of PDGFRα. Such approaches are well known in the art, and have been described. PDGFRα inhibition by such therapeutics may be confirmed, for example, by examining the ability of the compound to inhibit PDGFRα activity, but not other kinase activity, in a panel of kinases, and/or by examining the inhibition of PDGFRα activity in a biological sample comprising NSCLC tumor cells, as described above. Methods for identifying compounds that inhibit PDGFRα activity in NSCLC tumors are further described below.

Anti-Sense and/or Transcription Inhibitors.

PDGFRα-inhibiting therapeutics may also comprise antisense and/or transcription inhibiting compounds that inhibit PDGFRα activity by blocking transcription of the gene encoding PDGFRα. The inhibition of various receptor kinases, including VEGFR, EGFR, and IGFR, and FGFR, by antisense therapeutics for the treatment of cancer has been described. See, e.g., U.S. Pat. Nos. 6,734,017; 6,710,174, 6,617,162; 6,340,674; 5,783,683; 5,610,288.

Antisense oligonucleotides may be designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM.* pp. 40-46 (1990); Van Der Krol et al., *BioTechniques* 6(10): 958-976 (1988); Skorski et al., *Proc. Natl. Acad. Sci. USA* (1994) 91: 4504-4508. Inhibition of human carcinoma growth in vivo using an antisense RNA inhibitor of EGFR has recently been described. See U.S. Patent Publication No. 20040047847, "Inhibition of Human Squamous Cell Carcinoma Growth In vivo by Epidermal Growth Factor Receptor Antisense RNA Transcribed from a Pol III Promoter," Mar. 11, 2004, He et al. Similarly, a PDGFRα-inhibiting therapeutic comprising at least one antisense oligonucleotide against a mammalian PDGFRα gene may be prepared according to methods described above. Pharmaceutical compositions comprising PDGFRα-inhibiting antisense compounds may be prepared and administered as further described below.

Small Interfering RNA.

Small interfering RNA molecule (siRNA) compositions, which inhibit translation, and hence activity, of PDGFRα through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, "Composition and Method for Inhibiting Expression of a Target Gene," Feb. 26, 2004, Kreutzer et al.; U.S. Patent Publication No. 20020086356, "RNA Sequence-Specific Mediators of RNA Interference," Jun. 12, 2003, Tuschl et al.; U.S. Patent Publication 20040229266, "RNA Interference Mediating Small RNA Molecules," Nov. 18, 2004, Tuschl et. al.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g. Promega, Inc. (www.promega.com); Dharmacon, Inc. (www.dharmacon.com). Detailed technical manuals on the design, construction, and use of dsRNA for RNAi are available. See, e.g. Dharmacon's "RNAi Technical Reference & Application Guide"; Promega's "RNAi: A Guide to Gene Silencing." PDGFRα-inhibiting siRNA products are also commercially available, and may be suitably employed in the method of the invention. See, e.g. Dharmacon, Inc., Lafayette, Colo. (Cat Nos. M-003162-03, MU-003162-03, D-003162-07 thru -10 (siGENOMET™ SMARTselection and SMARTpool® siRNAs).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication No. 20040038921, Kreutzer et al., supra; U.S. Patent Publication No. 20040229266, Tuschl et al., supra. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891, Sep. 11, 2003, McSwiggen J. An algorithm for identifying and selecting RNAi target sites has also recently been described. See U.S. Patent Publication No. 20040236517, "Selection of Target Sites for Antisense Attack of RNA," Nov. 25, 2004, Drlica et al.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu et al. (1987), *Nucl. Acids Res.* 15: 1311; Fraley et al. (1980), *J. Biol. Chem.* 255: 10431; Capecchi (1980), *Cell* 22: 479). DNA may also be introduced into cells using cationic liposomes (Feigner et al. (1987), *Proc. Natl. Acad. Sci. USA* 84: 7413). Commercially available cationic lipid formulations include Tfx 50 (Promega) or Lipofectamin 200 (Life Technologies). Alternatively, viral vectors may be employed to deliver dsRNA to a cell and mediate RNAi. See U.S Patent Publication No. 20040023390, "siRNA-mediated Gene Silencing with Viral Vectors," Feb. 4, 2004, Davidson et al.

Transfection and vector/expression systems for RNAi in mammalian cells are commercially available and have been well described. See, e.g. Dharmacon, Inc., DharmaFECT™ system; Promega, Inc., siSTRIKET™ U6 Hairpin system; see also Gou et al. (2003) *FEBS.* 548, 113-118; Sui, G. et al. A DNA vector-based RNAi technology to suppress gene expression in mammalian cells (2002) *Proc. Natl. Acad. Sci.* 99, 5515-5520; Yu et al. (2002) *Proc. Natl. Acad. Sci.* 99, 6047-6052; Paul, C. et al. (2002) *Nature Biotechnology* 19, 505-508; McManus et al. (2002) *RNA* 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit PDGFRα expression and activity in a NSCLC tumor, by preparing a pharmaceutical preparation comprising a therapeutically-effective amount of such dsRNA, as described above, and administering the preparation to a human subject having a PDGFRα-activated NSCLC tumor, for example, via direct injection to the tumor. The similar inhibition of other receptor tyrosine kinases, such as VEGFR and EGFR using siRNA inhibitors has recently been described. See U.S. Patent Publication No. 20040209832, Oct. 21, 2004, McSwiggen et al.; U.S. Patent Publication No. 20030170891, Sep. 11, 2003, McSwiggen; U.S. Patent Publication No. 20040175703, Sep. 9, 2004, Kreutzer et al.

Therapeutic Compositions; Administration.

PDGFRα-inhibiting therapeutic compositions useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, a PDGFRα-inhibiting therapeutic will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consists exclusively of an aqueous buffer ("exclusively" means no auxiliary agents or encapsulating substances are present which might affect or mediate uptake of the PDGFRα-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

PDGFRα-inhibiting therapeutic compositions may also include encapsulated formulations to protect the therapeutic (e.g. a dsRNA compound) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

PDGFRα-inhibiting compositions can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, Trends Cell Bio., 2, 139; DELIVERY STRATEGIES FOR ANTISENSE OLIGONUCLEOTIDE THERAPEUTICS, ed. Akbtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

PDGFRα-inhibiting therapeutics can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262.

Pharmaceutically acceptable formulations of PDGFRα-inhibitory therapeutics include salts of the above described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (i.e. systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the PDGFRα-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, Fundam. Clin. Pharmacol., 13, 16-26); biodegradable polymers, such as poly (DL-lactide-coglycolide) microspheres for sustained release delivery after intracerebral implantation (Emerich et al, 1999, Cell Transplant, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuro-psychopharmacol Biol Psychiatry, 23, 941-949, 1999). Other non-limiting examples of delivery strategies for the PDGFRα-inhibiting compounds useful in the method of the invention include material described in Boado et al., 1998, J. Pharm. Sci., 87, 1308-1315; Tyler et al., 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

Therapeutic compositions comprising surface-modified liposomes containing poly (ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in REMINGTON'S PHARMACEUTICAL SCIENCES, Mack Publishing Co. (A. R. Gennaro edit. 1985). For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

A PDGFRα-inhibiting therapeutic useful in the practice of the invention may comprise a single compound as described above, or a combination of multiple compounds, whether in the same class of inhibitor (i.e. antibody inhibitor), or in different classes (i.e antibody inhibitors and small-molecule inhibitors). Such combination of compounds may increase the overall therapeutic effect in inhibiting the progression of a PDGFRα-expressing NSCLC tumor in the mammal. For example, the therapeutic composition may a small molecule inhibitor, such as STI-571 (Gleevec®) alone, or in combination with other Gleevec® analogues targeting PDGFRα activity and/or small molecule inhibitors of EGFR, such as Tarceva™ or Iressa™. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting PDGFRα activity and NSCLC tumor growth in vivo can be assessed as described below.

Identification of PDGFRα-Inhibiting Compounds.

The invention also provides, in part, a method for determining whether a compound inhibits the progression of a mammalian NSCLC tumor belonging to a subset of NSCLC tumors in which PDGFRα is activated, by determining whether the compound inhibits the activity of PDGFRα in the NSCLC tumor. In one preferred embodiment, inhibition of activity of PDGFRα is determined by examining a biological sample comprising cells from the NSCLC tumor. In another preferred embodiment, inhibition of activity of PDGFRα is determined using at least one PDGFRα activation state-specific reagent, and in one preferred embodiment, the activation-state specific reagent is a phosphorylation-site specific antibody.

The tested compound may be any type of therapeutic or composition as described above. Methods for assessing the efficacy of a compound, both in vitro and in vivo, are well established and known in the art. For example, a composition may be tested for ability to inhibit PDGFRα in vitro using a cell or cell extract in which PDGFRα is activated. A panel of compounds may be employed to test the specificity of the compound for PDGFRα (as opposed to other targets, such as EGFR or PDGFR beta).

A compound found to be an effective inhibitor of PDGFRα activity in vitro may then be examined for its ability to inhibit NSCLC tumor growth, in vivo, using, for example, mammalian xenografts harboring human PDGFRα-expressing NSCLC tumors. In this procedure, cell lines known to be driven by PDGFRa are placed subcutaneously in the mouse. The cells then grow into a tumor mass that may be visually monitored. The mouse may then be treated with the drug. The effect of the drug treatment on tumor size may be externally observed. The mouse is then sacrificed and the tumor removed for analysis by IHC and Western blot. In this way, the effects of the drug may be observed in a biological setting most closely resembling a patient. The drug's ability to alter signaling in the tumor cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Identification of PDGFRα-Expression in a NSCLC Cell Line by Global Phosphopeptide Profiling The global phosphorylation profiles of four human NSCLC cell lines, A549, H441, H1373, and H1703, were examined using a recently described and powerful technique for the isolation and mass spectrometric characterization of modified peptides from complex mixtures (the "IAP" technique, see Rush et al., supra). The IAP technique was performed using a phosphotyrosine-specific antibody (CELL SIGNALING TECHNOLOGY, INC., Beverly, Mass., 2003/04 Cat. #9411) to isolate, and subsequently characterize, phosphotyrosine-containing peptides from extracts of the NSCLC cell lines.

Tryptic phosphotyrosine-containing peptides were purified and analyzed from extracts of each of the cell lines mentioned above, as follows. Cells were cultured in DMEM medium or RPMI 1640 medium supplemented with 10% fetal bovine serum and penicillin/streptomycin. Cells were harvested by low speed centrifugation. After complete aspiration of medium, cells were resuspended in 1 mL lysis buffer per $1.25 \times 10^8$ cells (20 mM HEPES pH 8.0, 9 M urea, 1 mM sodium vanadate, supplemented or not with 2.5 mM sodium pyro-phosphate, 1 mM β-glycerol-phosphate) and sonicated.

Sonicated cell lysates were cleared by centrifugation at 20,000×g, and proteins were reduced with DTT at a final concentration of 4.1 mM and alkylated with iodoacetamide at 8.3 mM. For digestion with trypsin, protein extracts were diluted in 20 mM HEPES pH 8.0 to a final concentration of 2 M urea and soluble TLCK-trypsin (Worthington) was added at 10-20 µg/mL. Digestion was performed for 1-2 days at room temperature.

Trifluoroacetic acid (TFA) was added to protein digests to a final concentration of 1%, precipitate was removed by centrifugation, and digests were loaded onto Sep-Pak $C_{18}$ columns (Waters) equilibrated with 0.1% TFA. A column volume of 0.7-1.0 ml was used per $2 \times 10^8$ cells. Columns were washed with 15 volumes of 0.1% TFA, followed by 4 volumes of 5% acetonitrile (MeCN) in 0.1% TFA. Peptide fraction I was obtained by eluting columns with 2 volumes each of 8, 12, and 15% MeCN in 0.1% TFA and combining the eluates. Fractions II and III were a combination of eluates after eluting columns with 18, 22, 25% MeCN in 0.1% TFA and with 30, 35, 40% MeCN in 0.1% TFA, respectively. All peptide fractions were lyophilized.

Peptides from each fraction corresponding to $2 \times 10^8$ cells were dissolved in 1 ml of IAP buffer (20 mM Tris/HCl or 50 mM MOPS pH 7.2, 10 mM sodium phosphate, 50 mM NaCl) and insoluble matter (mainly in peptide fractions III) was removed by centrifugation. IAP was performed on each peptide fraction separately. The phosphotyrosine monoclonal antibody P-Tyr-100 (Cell Signaling Technology, Inc., catalog number 9411) was coupled at 4 mg/ml beads to protein G (Roche), respectively. Immobilized antibody (15 µl, 60 µg) was added as 1:1 slurry in IAP buffer to 1 ml of each peptide fraction, and the mixture was incubated overnight at 4° C. with gentle rotation. The immobilized antibody beads were washed three times with 1 ml IAP buffer and twice with 1 ml water, all at 4° C. Peptides were eluted from beads by incubation with 75 µl of 0.1% TFA at room temperature for 10 minutes.

Alternatively, one single peptide fraction was obtained from Sep-Pak C18 columns by elution with 2 volumes each of 10%, 15%, 20%, 25%, 30%, 35° A) and 40% acetonitirile in 0.1% TFA and combination of all eluates. IAP on this peptide fraction was performed as follows: After
lyophilization, peptide was dissolved in 1.4 ml IAP buffer (MOPS pH 7.2, 10 mM sodium phosphate, 50 mM NaCl) and insoluble matter was removed by centrifugation. Immobilized antibody (40 µl, 160 µg) was added as 1:1 slurry in IAP buffer, and the mixture was incubated overnight at 4° C. with gentle shaking. The immobilized antibody beads were washed three times with 1 ml IAP buffer and twice with 1 ml water, all at 4° C. Peptides were eluted from beads by incubation with 55 µl of 0.15% TFA at room temperature for 10 min (eluate 1), followed by a wash of the beads (eluate 2) with 45 µl of 0.15% TFA. Both eluates were combined.

Analysis by LC-MS/MS Mass Spectrometry.

40 µl or more of IAP eluate were purified by 0.2 µl StageTips or ZipTips. Peptides were eluted from the microcolumns with 1 µl of 40% MeCN, 0.1% TFA (fractions I and II) or 1 µl of 60% MeCN, 0.1% TFA (fraction III) into 7.6 µl of 0.4% acetic acid/0.005% heptafluorobutyric acid. For single fraction analysis, 1 µl of 60% MeCN, 0.1% TFA, was used for elution from the microcolumns. This sample was loaded onto a 10 cm×75 µm PicoFrit capillary column (New Objective) packed with Magic C18 AQ reversed-phase resin (Michrom Bioresources) using a Famos autosampler with an inert sample injection valve (Dionex). The column was then developed with a 45-min linear gradient of acetonitrile delivered at 200 nl/min (Ultimate, Dionex), and tandem mass spectra were collected in a data-dependent manner with an LCQ Deca XP Plus ion trap mass spectrometer.

Database Analysis & Assignments.

MS/MS spectra were evaluated using TurboSequest in the Sequest Browser package (v. 27, rev. 12) supplied as part of BioWorks 3.0 (ThermoFinnigan). Individual MS/MS spectra were extracted from the raw data file using the Sequest Browser program CreateDta, with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were performed against the NCBI human protein database (either as released on Apr. 29, 2003 and containing 37,490 protein sequences or as released on Feb. 23, 2004 and containing 27,175 protein sequences). Cysteine carboxamidomethylation was specified as a static modification, and phosphorylation was allowed as a variable modification on serine, threonine, and tyrosine residues or on tyrosine residues alone. It was determined that restricting phosphorylation to tyrosine residues had little effect on the number of phosphorylation sites assigned.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., *Mol. Cell. Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site.

For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain a series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of assigned sequences (not shown here) were reviewed by at least three scientists to establish their credibility.

The foregoing IAP analysis identified six phospho-tyrosine sites in PDGFRα as being present in the H1703 cell line, but not in the three other NSCLC cell lines examined (see Table 1 below). In contrast, phospho-tyrosine sites in EGFR were identified in all four cell lines. This result was surprising since the link between PDGFRα expression and/or phosphorylation in a subset of human NSCLC had not previously been established.

include both the cell line and the surrounding stomal cells. As a result, these samples are expected to include both isoforms. The results demonstrate that the CST (Cell Signaling Technology, Beverly, Mass.) PDGFRα and PDGFRβ antibodies (Cat. Nos. 3164 and 3169, respectively) correctly detect the appropriate proteins and do not detect any other proteins as shown by the lack of additional bands on the Western blot. In contrast, the PDGFRα antibody from Santa Cruz Biotechnology (Santa Cruz, Calif.) (Cat. No. SC-338) detects multiple proteins. Some of the proteins detected with this antibody are detected as strongly as the bands at the correct molecular weight (see FIG. 4). While Santa Cruz Biotechnology offers multiple antibodies to PDGFRα, SC-338 is the preferred product for IHC and is the product most often referenced in the literature.

A previous report (Zhang et al., (2003), supra.) employed a PDGFRα antibody (from Santa Cruz Biotechnology, Inc.) in an attempt to analyze PDGFRα expression in the A549 cell line. This Western blot was presently repeated using the SC-338 antibody from Santa Cruz Biotechnology as well as a CST antibody to PDGFRα and a CST antibody to PDGFRβ (results are shown in FIG. 5(a)). The NIH3T3 cell line was included as a positive control, as it is known that this cell line expresses both isoforms of PDGFR. The results indicate that the Santa Cruz Biotechnology antibody detects multiple proteins in the A549 cells, none of which match the correct molecular weight for PDGFR. The antibody does detect a protein in the NIH3T3 cells that has the correct molecular weight. The CST PDGFRα (#3164) antibody detects a pro-

TABLE 1

| Kinase | Phosphorylation Site Sequence | Phosphorylated Tyrosine | SEQ ID NO: |
|---|---|---|---|
| PDGFRα | VIESISPDGHEyIYVDPMQLPYDSR | Y572 | SEQ ID NO: 3 |
| PDGFRα | QADTTQyVPMLER | Y742 | SEQ ID NO: 4 |
| PDGFRα | SLyDRPASYK | Y762 | SEQ ID NO: 5 |
| PDGFRα | SLYDRPASyK | Y768 | SEQ ID NO: 6 |
| PDGFRα | DIMHDSNyVSK | Y849 | SEQ ID NO: 7 |
| PDGFRα | LSADSGyIIPLPDIDPVPEEEDLGKR | Y1018 | SEQ ID NO: 8 |

EXAMPLE 2

Western Blot Analysis and IHC of PDGFRα Expression in NSCLC Tumor Cell Lines and Xenografts The observation that the H1703 NSCLC tumor cell line—but not the other NSCLC cell lines—expresses PDGFRα was confirmed by Western blot analysis of cell extracts using antibodies specific for PDGFRα and other receptor tyrosine kinases (RTKs) and downstream kinases. Antibody specificity for receptor tyrosine kinases is often difficult to obtain due to many possible variables including the close homology among the receptors and the secondary modifications that the receptors undergo. Therefore, the first step in determining PDGFRα expression by Western blot analysis was to identify an antibody that is specific for this protein.

Figure 4:
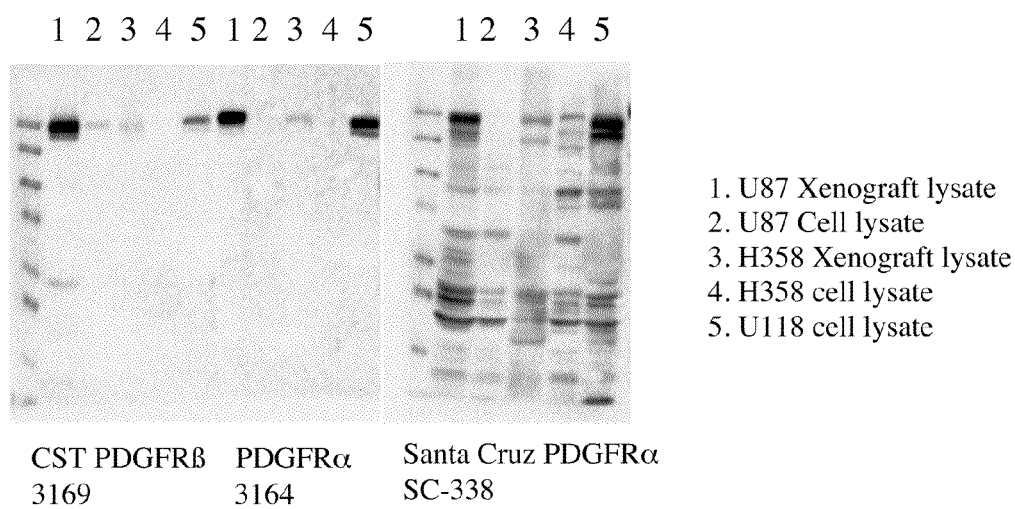
FIG. 4—consists of a Western blot analysis of extracts from human NSCLC cell lines using various antibodies made against PDGFRα, demonstrating that some commercially available antibodies are not in fact specific for PDGFRα.

FIG. 4 presents the results of an analysis of three cell lines probed with two antibodies to PDGFRα and one antibody to PDGFRβ. The U87 cell line is known to express PDGFRβ, the H358 cell line does not express PDGFR and the H118 cell line strongly expresses both isoforms. The xenograft samples tein with the correct molecular weight in the NIH3T3 cell line but not in the A549 cells. Likewise, the CST PDGFRβ (#3169) antibody detects PDGFRβ in the NIH3T3 cell line but not in the A549 cell line. These results clearly demonstrate that the Santa Cruz antibody is not specific for PDGFRα in the A549 cell line, and that Westerns with antibodies that are specific for this protein indicate that the A549 cell line does not express detectable levels of PDGFRα. The present results bring into doubt the conclusions reached by Zhang et al., and given the lack of specificity of the antibody employed in that study, it is likely the authors detected something other than PDGFRα expression.

The initial mass spec screen of NSCLC cell lines indicated that the H1703 cell line expressed PDGFRα (see Example 1). The CST PDGFR antibodies that have been shown to be specific were used in Western blot analysis of this cell line in FIG. 5b. The A549 cell line was also included in the analysis as well as two Santa Cruz Biotechnology PDGFRα antibodies (SC-338 and SC-431). The results support the mass spec result, indicating that the H1703 cell line expresses PDGFRα while the A549 cell line does not. The results with the Santa Cruz Biotechnology antibodies are similar although both antibodies show multiple cross-reactive bands in the A549 cell line.

As a final determination of PDGFRα expression, the cells were stimulated with PDGFaa growth factor. This homodimer of the a form of the growth factor specifically activates PDGFRα and not PDGFRβ. Therefore, cells that express PDGFRα should show phosphorylation of the receptor and activation of downstream signaling following treatment with this ligand, while cells that lack the receptor should not show a response. AKT phosphorylation was used as a marker of downstream signaling.

Figure 6:
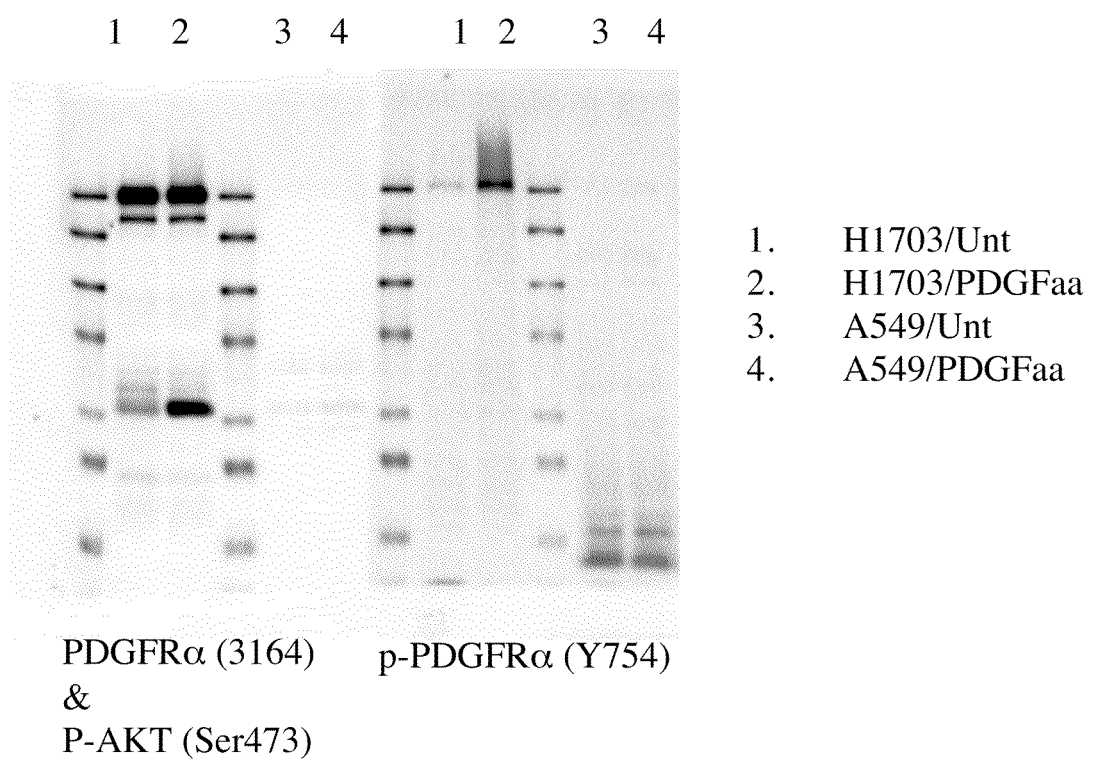
FIG. 6—is a Western blot analysis of extracts from two NSCLC cell lines induced with PDGFaa using antibodies made against PDGFRα, phospho-PDGFRα and for the downstream kinase, phospho-AKT, demonstrating that the H1703 cell line expresses PDGFRα that may be activated by PDGFaa while the A549 cell line does not express the receptor and is not responsive to PDGFaa.

The results in FIG. 6 show that in the H1703 cell line, PDGFaa treatment results in phosphorylation of PDGFRα and AKT. PDGFaa treatment of A549 cells does not result in AKT activation and no PDGFRα or phospho-PDGFRα is detected. These results, along with the results presented above, clearly demonstrate that the H1703 cell line expresses PDGFRα while the A549 cell line does not.

Finally, the antibody specificity observed by Western blot analysis may have significant implications for the use of the antibody in IHC. To test the use of the PDGFRα antibodies in IHC, A549 xenografts were formalin fixed and paraffin embedded, and probed with the antibodies. FIG. 7 presents the IHC results.

As expected from the Western blot results, the Santa Cruz PDGFRα antibody, SC-338, gives non-specific staining of the A549 cells while the CST #3164 antibody only detects PDGFRα in the surrounding stromal cells. This staining of the normal mouse stomal cells is appropriate as these cells are known to express the receptor.

EXAMPLE 3

Immunohistochemical Analysis of PDGFRα Expression in Human NSCLC Tumor Samples

The existence of a distinct subset of human NSCLC tumors in which PDGFRα is expressed was further confirmed by IHC analysis of multiple tissue micro-arrays comprising tumor samples from 304 human NSCLC patients. Tissues were obtained from multiple sources including commercial as well as public tissue banks. The classification of the tumors as well as the scoring of the IHC staining was performed by a trained pathologist. The IHC was done with the CST PDGFRα-specific antibody (#3164) that was shown to be specific by Western blot as well as peptide absorption (data not shown). The results of the IHC screen are summarized in Table 2 below.

TABLE 2

PDGFRα is Expressed in a Small Subset of Human NSCLC Tumors.

| Cases | IHC score | Pathological diagnosis | Age | Sex |
|---|---|---|---|---|
| HL001 | 2+ | Adenocarcinoma | 40 | F |
| HL002 | 2+ | Adenocarcinoma | 62 | F |
| HL003 | 1-2+ | Adenocarcinoma | 52 | M |
| HL004 | 1+ | Adenocarcinoma | 51 | F |
| HL005 | 1+ | Adenocarcinoma | 60 | F |
| HL006 | 2+ | Adenocarcinoma | 50 | M |
| HL007 | 1-2+ | Adenocarcinoma | 56 | F |
| HL008 | 1-2+ | Bronchioloalveolar carcinoma | 58 | M |
| HL009 | 3+ | Bronchioloalveolar carcinoma | 57 | F |
| HL010 | 2-3+ | Bronchioloalveolar carcinoma | 52 | F |
| HL011 | 1-2+ | Bronchioloalveolar carcinoma | 54 | M |
| HL012 | 1+ | Bronchioloalveolar carcinoma | 52 | F |
| HL013 | 1+ | Bronchioloalveolar carcinoma | 48 | F |
| HL014 | 1+ | Squamous cell carcinoma | 67 | M |
| HL015 | 1+ | mucoeperdoid carcinoma | 26 | F |
| HL016 | 1-2+ | adenoid carcinoma | 54 | F |
| HL017 | 3+ | Sarcomatoid carcinoma | 59 | M |

As shown in Table 2, out of 304 NSCLC tumor tissue samples screened, only 17 (6%) showed positive PDGFRα staining. PDGFRα expression was seen more frequently in Bronchioloalveolar carcinomas (6 cases) and Adenocarcinomas (7 cases) (13/17, 76%), and less frequently in Sarcomatoid carcinomas (1 case) (1/17, 6%). PDGFRα-expressing NSCLC tumors occur more frequently in women (11/17, 65%) than in men (6/17, 35%). These results are very different than the IHC results reported by Zhang et al. (2003), supra., and reflect the specificity of the CST PDGFRα antibody compared to the non-specific Santa Cruz Biotechnology antibody. Zhang et al. reported PDGFRα expression in 27 out of 29 NSCLC samples. This extremely high level of staining reported in the Zhang study is most likely is due to the cross-reactivity of the antibody employed in the IHC analysis. It is noteworthy that, prior to the present disclosure, no other reports of PDGFRα expression in NSCLC have been made following the Zhang et al. paper.

EXAMPLE 4

Gleevec® Inhibits Growth of PDGFRα-Expressing Mammalian NSCLC Cell Lines

In order to confirm that PDGFRα is driving cell growth and survival in the subset of NSCLC tumors in which this RTK is expressed, the ability of a PDGFRα-inhibitor, Gleevec®, to inhibit growth of H1703 cells was examined. A standard MTT cell proliferation assay (see Mosmann, *J. Immunol. Methods.* 65(1-2): 55-63 (1983)) was performed on the H1703, A549, H1373 and K562 cell lines using a range of Gleevec® concentrations. The H1373 cell line was predicted to be insensitive to Gleevec® as it is thought to be driven by erbB2 and erbB3 (see Sithanandam, *Carcinogenesis* 24(10): 1581-92 (2003)). The K562 cell line is known to be driven by the BCR/ABL translocation which is inhibited by Gleevec®. The results of the assay are presented in FIG. 8(a). As predicted, the H1373 cell line is insensitive to Gleevec® while the K562 cell line is sensitive at concentrations of 0.1 μM. The H1703 cell line was also sensitive to Gleevec® at concentrations similar to what was observed with the K562 cell line. In contrast, the A549 cell line was not affected by Gleevec® at concentrations up to 10 μM.

To confirm the effect of Gleevec® on the H1703 cell line, Western blot analysis was performed on the cells following exposure to a range of Gleevec® concentrations. FIG. 8(b) presented the results of this analysis. As shown, increasing Gleevec® concentrations result in an increase in cleaved PARP, an indication that Gleevec® treatment is resulting in cell apoptosis. PARP cleavage is one mechanism known to be involved in cell apoptosis (see Lazebnik et al. *Nature* 371: 346-347 (1994)). Cell apoptosis was also analyzed by analyzing caspase 3 cleavage by flow cytometry of the cells following Gleevec® treatment for 1, 2 or 3 days. As shown in FIG. 8(c), caspase 3 cleavage is observed as early as 1 day of treatment and increases as the exposure time increases. Similar to PARP cleavage, caspase 3 cleavage is a well known marker of cell apoptosis (see Fernandes-Alnemri et al., *J. Biol. Chem.* 269: 30761-30764 (1994)). These results demonstrate that Gleevec® treatment of H1703 cells results in growth inhibition and apoptosis.

EXAMPLE 5

Gleevec® Inhibits Signaling in PDGFRα-Expressing Mammalian NSCLC Cell Lines

If Gleevec® alters the ability of PDGFRα to drive cell proliferation and survival in H1703 cells, then it must interfere with the cellular signaling that occurs downstream of the receptor. To test this hypothesis, Western blot analysis was performed on the cells following Gleevec® treatment as well as Iressa™ treatment and stimulation with EGF. Iressa™ is a targeted EGFR inhibitor. Phosphorylation of the EGFR receptor, ERK and AKT were determined while total PDGFRα and ERK1/2 are included as loading controls. FIG. 9(a) presents the results of this analysis. In the untreated control cells, AKT and ERK are both phosphorylated while the EGFR receptor is not. EGF treatment induces the phosphorylation of EGFR as well as an increase in phosphorylation of ERK and AKT as would be expected. Treatment with Iressa™ decreases the phosphorylation of EGFR and ERK but not AKT. Importantly, only treatment of the cells with Gleevec® results in the loss of AKT phosphorylation. AKT is thought to be the primary driver of cell survival (see Franke, *Cell* 88: 435-437 (1997)).

Therefore, these results demonstrate that while these cells express EGFR that may be inhibited by Iressa™, the constitutive activation of AKT is only inhibited through PDGFRα. FIG. 9(b) presents a dose response analysis of Gleevec® on H1703 cells. The results indicate that Gleevec® treatment at doses as low as 0.01 μM inhibit PDGFRα phosphorylation while doses of 0.1 μM greatly inhibit AKT phosphorylation. These results are consistent with the hypothesis that Gleevec® is inhibiting H1703 cell growth and survival through inhibition of PDGFRα and AKT signaling.

EXAMPLE 6

Gleevec® Inhibits Growth of PDGFRα-Expressing Mammalian NSCLC Tumor Xenografts

In order to further confirm the ability of Gleevec® to inhibit cell growth and survival in the subset of NSCLC tumors in which this RTK is expressed, human tumor xenografts, in vivo, were examined. In this model, human cell lines are injected into immune-compromised mice forming xenograft tumors that resemble human tumors including vascularization and other features found in human tumors. The mice are then administered the drug in the same manner as in human patients. Tumor size may be monitored visually during drug treatment and the tumors may be removed, fixed and analyzed by standard IHC procedures or lysed and analyzed by Western blot.

FIG. 10(a) presents the results of the xenograft experiments demonstrating that Gleevec® treatment results in a significant decrease in tumor size. The average tumor diameter in the 5 control mice was approximately 190 mm while the average tumor diameter in the 3 treated mice was only approximately 20 mm. This dramatic decrease in tumor size in the treated mice is a strong indication that Gleevec® treatment in vivo has a therapeutic effect on tumors that are driven by PDGFRα.

Figure 11:
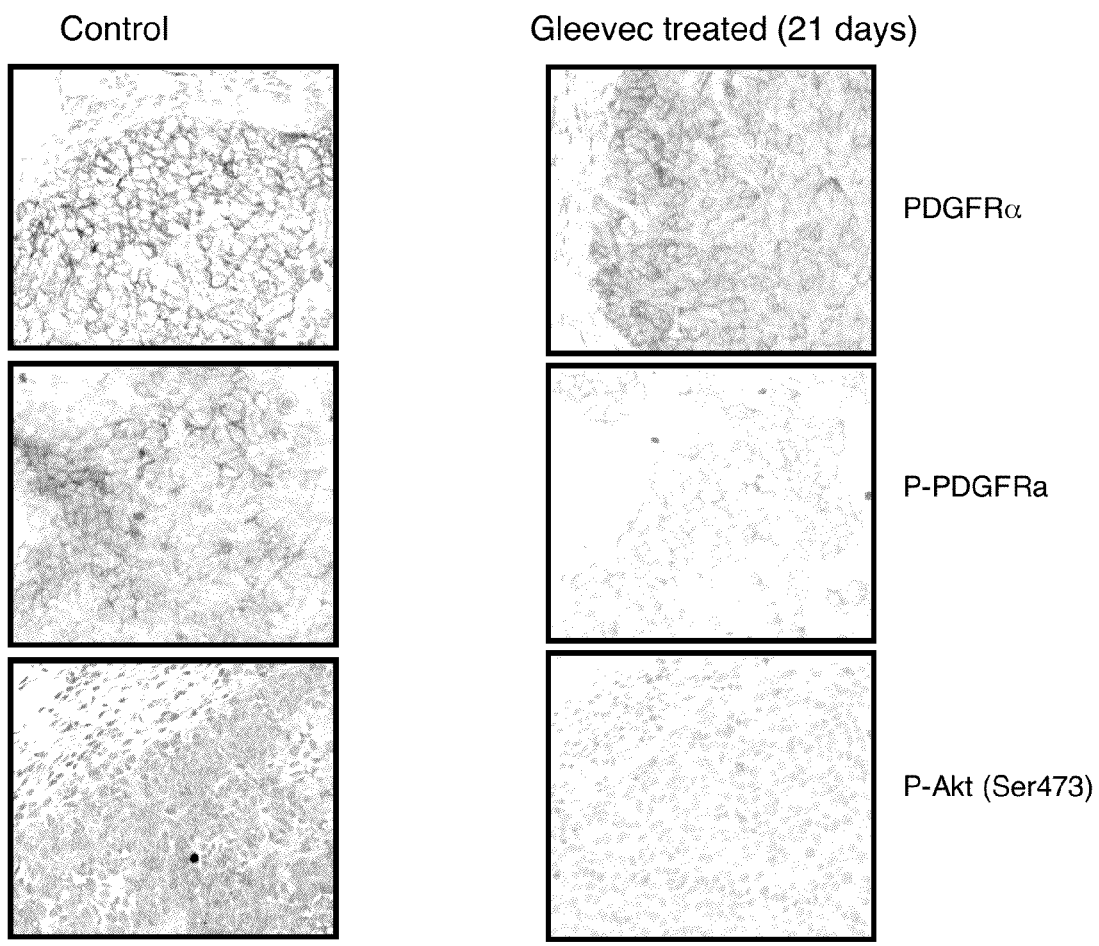
FIG. 11—is an immunohistochemical (IHC) analysis of cells from mouse NSCLC tumor xenografts (expressing PDGFRα) either treated (panel B) or untreated (panel A) with the PDGFRα-inhibitor Gleevec® (STI-571) demonstrating that exposure to Gleevec results in a significant decrease in phosphorylation of PDGFRα and AKT while the total level of the receptor does not change.

To further analyze the mechanism behind this reduction in tumor size, Western blots were performed on the tumor lysate from 4 treated mice compared to one control mouse. The results in FIG. 10(b) show that in these xenografts, Gleevec® is inhibiting PDGFRα phosphorylation (total AKT was included in the Western as a loading control). These results are consistent with previous results that suggest that Gleevec® is reducing tumor size through PDGFRα inhibition. The xenograft tumors were also analyzed by IHC (see FIG. 11) in which control tumors were compared to Gleevec® treated tumors. The results of the IHC analysis again demonstrate that Gleevec® treatment results in a decrease in PDGFRα and AKT phosphorylation. The IHC results suggest that mammalian tumors, e.g. from a human patient, may be analyzed by IHC in a similar manner to determine the biological activity of a PDGFRα inhibitor.

What is claimed is:

1. A method for inhibiting the progression of a mammalian non-small cell lung cancer (NSCLC) tumor belonging to a subset of NSCLC tumors in which PDGFRα is expressed, said method comprising (a) determining if a mammalian NSCLC tumor expresses PDGFRα and (b) if said tumor expresses PDGFRα, contacting said tumor with a PDGFRα-inhibiting therapeutic selected from the group consisting of Imatinib mesylate (STI-571), BAY 43-93006, XL-999 and SU11248.

2. The method of claim 1, wherein the PDGFRα-inhibiting therapeutic is Imatinib mesylate (STI-571).

3. The method of claim 1, wherein the PDGFRα-inhibiting therapeutic is BAY 43-93006.

4. The method of claim 1, wherein the mammalian NSCLC tumor is a human NSCLC tumor.

5. The method of claim 1, wherein the PDGFRα-inhibiting therapeutic is XL-999.

6. The method of claim 1, wherein the PDGFRα-inhibiting therapeutic is SU11248.

7. The method of claim 2, wherein the mammalian NSCLC tumor is a human NSCLC tumor.

8. The method of claim 3, wherein the mammalian NSCLC tumor is a human NSCLC tumor.

9. The method of claim 5, wherein the mammalian NSCLC tumor is a human NSCLC tumor.

10. The method of claim 6, wherein the mammalian NSCLC tumor is a human NSCLC tumor.

* * * * *

SEQUENCE LISTING

```
<160> NUMBER OF SEQ ID NOS: 8

<210> SEQ ID NO 1
<211> LENGTH: 1089
<212> TYPE: PRT
<213> ORGANISM: Homo sapiens

<400> SEQUENCE: 1

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80
```

-continued

```
Phe Val Thr Val Leu Glu Val Ser Ser Ala Ser Ala Ala His Thr Gly
             85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp Asp
130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
            165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
            195                 200                 205

Lys Ala Thr Ser Glu Leu Asp Leu Glu Met Glu Ala Leu Lys Thr Val
            210                 215                 220

Tyr Lys Ser Gly Glu Thr Ile Val Thr Cys Ala Val Phe Asn Asn
225                 230                 235                 240

Glu Val Val Asp Leu Gln Trp Thr Tyr Pro Gly Glu Val Lys Gly Lys
            245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
            290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
            325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
            370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
            405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
            435                 440                 445

Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
            485                 490                 495

Ile Ala Val Arg Cys Leu Ala Lys Asn Leu Leu Gly Ala Glu Asn Arg
            500                 505                 510
```

-continued

```
Glu Leu Lys Leu Val Ala Pro Thr Leu Arg Ser Glu Leu Thr Val Ala
        515                 520                 525

Ala Ala Val Leu Val Leu Val Ile Val Ile Ile Ser Leu Ile Val
530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
```

```
                     930             935             940
His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
                980                 985                 990

Tyr Lys Asn Glu Glu Asp Lys Leu  Lys Asp Trp Glu Gly  Gly Leu Asp
            995                 1000                1005

Glu Gln  Arg Leu Ser Ala Asp  Ser Gly Tyr Ile Ile  Pro Leu Pro
     1010                1015                1020

Asp Ile  Asp Pro Val Pro Glu  Glu Glu Asp Leu Gly  Lys Arg Asn
     1025                1030                1035

Arg His  Ser Ser Gln Thr Ser  Glu Glu Ser Ala Ile  Glu Thr Gly
     1040                1045                1050

Ser Ser  Ser Ser Thr Phe Ile  Lys Arg Glu Asp Glu  Thr Ile Glu
     1055                1060                1065

Asp Ile  Asp Met Met Asp Asp  Ile Gly Ile Asp Ser  Ser Asp Leu
     1070                1075                1080

Val Glu  Asp Ser Phe Leu
     1085

<210> SEQ ID NO 2
<211> LENGTH: 4019
<212> TYPE: DNA
<213> ORGANISM: Homo Sapiens

<400> SEQUENCE: 2
ttctccccgc cccccagttg ttgtcgaagt ctggggggttg ggactggacc ccctgattgc      60
gtaagagcaa aaagcgaagg cgcaatctgg acactgggag attcggagcg cagggagttt     120
agagaaactt ttattttgaa gagaccaagg ttgagggggg gcttatttcc tgacagctat     180
ttacttagag caaatgatta gttttagaag gatggactat aacattgaat caattacaaa     240
acgcggtttt tgagcccatt actgttggag ctacaggag agaaacagga ggagactgca      300
agagatcatt tgggaaggcc gtgggcacgc tctttactcc atgtgtggga cattcattgc     360
ggaataacat cggaggagaa gtttcccaga gctatgggaa cttcccatcc ggcgttcctg     420
gtcttaggct gtcttctcac agggctgagc ctaatcctct gccagctttc attaccctct     480
atccttccaa atgaaaatga aaaggttgtg cagctgaatt catccttttc tctgagatgc     540
tttggggaga gtgaagtgag ctggcagtac cccatgtctg aagaagagag ctccgatgtg     600
gaaatcagaa atgaagaaaa caacagcggc ctttttgtga cggtcttgga agtgagcagt     660
gcctcggcgg cccacacagg gttgtacact tgctattaca accacactca gacagaagag     720
aatgagcttg aaggcaggca catttacatc tatgtgccag cccagatgt agcctttgta     780 cctctaggaa tgacggatta tttagtcatc gtggaggatg atgattctgc cattataccct    840 tgtcgcacaa ctgatcccga gactcctgta accttacaca cagtgagggg ggtggtacct    900
gcctcctacg acagcagaca gggctttaat ggaccttca ctgtagggcc ctatatctgt     960
gaggccaccg tcaaaggaaa gaagttccag accatcccat taatgtttta tgctttaaaa    1020
gcaacatcag agctggatct agaaatggaa gctcttaaaa ccgtgtataa gtcaggggaa    1080
acgattgtgg tcacctgtgc tgttttttaac aatgaggtgg ttgaccttca atggacttac    1140
cctggagaag tgaaaggcaa aggcatcaca atgctggaag aaatcaaagt cccatccatc    1200
```

```
aaattggtgt acactttgac ggtccccgag ccacggtga agacagtgg agattacgaa    1260
tgtgctgccc gccaggctac cagggaggtc aaagaaatga agaaagtcac tatttctgtc    1320
catgagaaag gtttcattga aatcaaaccc accttcagcc agttggaagc tgtcaacctg    1380
catgaagtca acattttgt tgtagaggtg cgggcctacc cacctcccag gatatcctgg    1440
ctgaaaaaca atctgactct gattgaaaat ctcactgaga tcaccactga tgtggaaaag    1500
attcaggaaa taaggtatcg aagcaaatta aagctgatcc gtgctaagga agaagacagt    1560
ggccattata ctattgtagc tcaaaatgaa gatgctgtga gagctatac ttttgaactg    1620
ttaactcaag ttccttcatc cattctggac ttggtcgatg atcaccatgg ctcaactggg    1680
ggacagacgg tgaggtgcac agctgaaggc acgccgcttc ctgatattga gtggatgata    1740
tgcaaagata ttaagaaatg taataatgaa acttcctgga ctattttggc caacaatgtc    1800
tcaaacatca tcacggagat ccactcccga gacaggagta ccgtggaggg ccgtgtgact    1860
ttcgccaaag tggaggagac catcgccgtg cgatgcctgg ctaagaatct ccttggagct    1920
gagaaccgag agctgaagct ggtggctccc accctgcgtt ctgaactcac ggtggctgct    1980
gcagtcctgg tgctgttggt gattgtgatc atctcactta ttgtcctggt tgtcatttgg    2040
aaacagaaac cgaggtatga aattcgctgg agggtcattg aatcaatcag cccggatgga    2100
catgaatata tttatgtgga cccgatgcag ctgcccttatg actcaagatg ggagtttcca    2160
agagatggac tagtgcttgg tcgggtcttg gggtctggag cgtttgggaa ggtggttgaa    2220
ggaacagcct atggattaag ccggtcccaa cctgtcatga agttgcagt gaagatgcta    2280
aaacccacgg ccagatccag tgaaaaacaa gctctcatgt ctgaactgaa gataatgact    2340
cacctggggc acatttgaa cattgtaaac ttgctgggag cctgcaccaa gtcaggcccc    2400
atttacatca tcacagagta ttgcttctat ggagatttgg tcaactattt gcataagaat    2460
agggatagct tcctgagcca ccacccagag aagccaaaga aagagctgga tatctttgga    2520
ttgaaccctg ctgatgaaag cacacggagc tatgttattt tatcttttga aaacaatggt    2580
gactacatgg acatgaagca ggctgatact acacagtatg tccccatgct agaaaggaaa    2640
gaggtttcta atattccga catccagaga tcactctatg atcgtccagc tcatataag    2700
aagaaatcta tgttagactc agaagtcaaa aacctccttt cagatgataa ctcagaaggc    2760
cttactttat tggatttgtt gagcttcacc tatcaagttg cccgaggaat ggagtttttg    2820
gcttcaaaaa attgtgtcca ccgtgatctg gctgctcgca acgtcctcct ggcacaagga    2880
aaaattgtga agatctgtga ctttggcctg gccagagaca tcatgcatga ttcgaactat    2940
gtgtcgaaag gcagtacctt tctgcccgtg aagtggatgg ctcctgagag catctttgac    3000
aacctctaca ccacactgag tgatgtctgg tcttatggca ttctgctctg ggagatcttt    3060
tcccttggtg gcaccccctta ccccggcatg atggtggatt ctactttcta caataagatc    3120
aagagtgggt accggatggc caagcctgac cacgctacca gtgaagtcta cgagatcatg    3180
gtgaaatgct ggaacagtga gccggagaag agaccctcct tttaccacct gagtgagatt    3240
gtggagaatc tgctgcctgg acaatataaa aagagttatg aaaaaattca cctgacttc    3300
ctgaagagtg accatcctgc tgtggcacgc atgcgtgtgg actcagacaa tgcatacatt    3360
ggtgtcacct acaaaaacga ggaagacaag ctgaaggact gggagggtgg tctggatgag    3420
cagagactga gcgctgacag tggctacatc attcctctgc ctgacattga ccctgtccct    3480
gaggaggagg acctgggcaa gaggaacaga cacagctcgc agacctctga agagagtgcc    3540
attgagacgg gttccagcag ttccaccttc atcaagagag aggacgagac cattgaagac    3600
```

```
atcgacatga tggacgacat cggcatagac tcttcagacc tggtggaaga cagcttcctg    3660
taactggcgg attcgagggg ttccttccac ttctggggcc acctctggat cccgttcaga    3720
aaaccacttt attgcaatgc ggaggttgag aggaggactt ggttgatgtt taaagagaag    3780
ttcccagcca agggcctcgg ggagcgttct aaatatgaat gaatgggata ttttgaaatg    3840
aactttgtca gtgttgcctc tcgcaatgcc tcagtagcat ctcagtggtg tgtgaagttt    3900
ggagatagat ggataaggga ataataggcc acagaaggtg aactttgtgc ttcaaggaca    3960
ttggtgagag tccaacagac acaatttata ctgcgacaga acttcagcat tgtaattat     4019
```

<210> SEQ ID NO 3
<211> LENGTH: 25
<212> TYPE: PRT
<213> ORGANISM: Homo sapiens

<400> SEQUENCE: 3

```
Val Ile Glu Ser Ile Ser Pro Asp Gly His Glu Tyr Ile Tyr Val Asp
1               5                   10                  15

Pro Met Gln Leu Pro Tyr Asp Ser Arg
            20                  25
```

<210> SEQ ID NO 4
<211> LENGTH: 13
<212> TYPE: PRT
<213> ORGANISM: Homo sapiens

<400> SEQUENCE: 4

```
Gln Ala Asp Thr Thr Gln Tyr Val Pro Met Leu Glu Arg
1               5                   10
```

<210> SEQ ID NO 5
<211> LENGTH: 10
<212> TYPE: PRT
<213> ORGANISM: Homo sapiens

<400> SEQUENCE: 5

```
Ser Leu Tyr Asp Arg Pro Ala Ser Tyr Lys
1               5                   10
```

<210> SEQ ID NO 6
<211> LENGTH: 10
<212> TYPE: PRT
<213> ORGANISM: Homo sapiens

<400> SEQUENCE: 6

```
Ser Leu Tyr Asp Arg Pro Ala Ser Tyr Lys
1               5                   10
```

<210> SEQ ID NO 7
<211> LENGTH: 11
<212> TYPE: PRT
<213> ORGANISM: Homo sapiens

<400> SEQUENCE: 7

```
Asp Ile Met His Asp Ser Asn Tyr Val Ser Lys
1               5                   10
```

<210> SEQ ID NO 8
<211> LENGTH: 26
<212> TYPE: PRT
<213> ORGANISM: Homo sapiens

<400> SEQUENCE: 8

```
Leu Ser Ala Asp Ser Gly Tyr Ile Ile Pro Leu Pro Asp Ile Asp Pro
1               5                   10                  15
Val Pro Glu Glu Glu Asp Leu Gly Lys Arg
                20              25
```